United States Patent
Oliver et al.

(10) Patent No.: US 9,487,813 B2
(45) Date of Patent: Nov. 8, 2016

(54) ANTIFUNGAL TARGET

(75) Inventors: Jason David Oliver, Wilmslow (GB); Katharine Sarah Dobb, Manchester (GB); Sarah Jane Kaye, London (GB); John Leslie Thain, Manchester (GB); Daniel Scott Tuckwell, Glossop (GB); Michael John Bromley, Halifax (GB)

(73) Assignee: F2G LTD, Manchester (GB)

( * ) Notice: Subject to any disclaimer, the term of this patent is extended or adjusted under 35 U.S.C. 154(b) by 1032 days.

(21) Appl. No.: 13/376,172

(22) PCT Filed: Jun. 4, 2010

(86) PCT No.: PCT/GB2010/001091
§ 371 (c)(1),
(2), (4) Date: Apr. 16, 2012

(87) PCT Pub. No.: WO2010/139952
PCT Pub. Date: Dec. 9, 2010

(65) Prior Publication Data
US 2012/0196763 A1    Aug. 2, 2012

(30) Foreign Application Priority Data
Jun. 5, 2009 (GB) .................................. 0909743.7

(51) Int. Cl.
C12Q 1/18 (2006.01)
C12N 9/12 (2006.01)
G01N 21/64 (2006.01)

(52) U.S. Cl.
CPC .............. C12Q 1/18 (2013.01); C12N 9/1288 (2013.01)

(58) Field of Classification Search
None
See application file for complete search history.

(56) References Cited

U.S. PATENT DOCUMENTS

2003/0138879 A1* 7/2003 Lambalot et al. ............... 435/47
2008/0305958 A1* 12/2008 Hayward ............................ 506/4

FOREIGN PATENT DOCUMENTS

| EP | 1 795 608 A1 | 6/2007 |
|---|---|---|
| JP | 2003-524144 A | 8/2003 |
| WO | WO-99/15894 A2 | 4/1999 |
| WO | WO-99/15894 A3 | 4/1999 |
| WO | WO-02/053728 A2 | 7/2002 |
| WO | WO-03/080828 A2 | 10/2003 |
| WO | WO-2006/060839 A2 | 6/2006 |
| WO | WO-2009/092808 A1 | 7/2009 |

OTHER PUBLICATIONS

Chalfie et al. Green fluorescent protein as a marker for gene expression. Science. Feb. 11, 1994;263(5148):802-5.*
Brody, S. et al. (1997). "Mitochondrial Acyl Carrier Protein is Involved in Lipoic Acid Syntheis in *Saccharomyces Cerevisiae*," *Febs Letters* 408:217-220.
Care, R.S. et al. (1999). "The *MET3* Promoter: A New Tool for *Candida albicans* Molecular Genetics," *Molecular Microbiology* 34(4):792-798.
Copp, J.N. et al. (Apr. 2006). "The Phosphopantheinyl Transferase Superfamily: Phylogenetic Analysis and Functional Implications on Cyanobacteria," *Applied and Environmental Microbiology* 72(4):2298-2305.
Dennison, P.M.J. et al. (2005). "Gene Disruption in *Candida albicans* Using a Synthetic, Codon-Optimised Cre-*loxP* System," *Fungal Genetics and Biology* 42:737-748.
GenBank Accession No. Q5APF3_CANAL, created on Apr. 26, 2005, located at <http://srs.ebi.ac.uk/srsbin/cgi-bin/wgetz?-e+[uniprot-id: Q5APF3_CANAL>, last visited on Sep. 14, 2010.
GenBank Accession No. A1CQZ9_ASPCL, created on Jan. 23, 2007, located at <http://srs.ebi.ac.uk/srsbin/cgi-bin/wgetz?-e+[uniprot-id: A1CQZ9_ASPCL]>, last visited on Sep. 14, 2010, 2 pages.
GenBank Accession No. B0YEF2_ASPFC, created on Apr. 8, 2008, located at <http://srs.ebi.ac.uk/srsbin/cgi-bin/wgetz?-e+[uniprot-id:B0YEF2_ASPFC]>, last visited on Sep. 14, 2010, 2 pages.
La Clair, J.J. et al. (2004). "Manipulation of Carrier Proteins in Antibiotic Biosynthesis," *Chemistry & Biology* 11:195-201.
Lambalot, R.H. (Oct. 20, 1995). "Cloning Overproduction, and Characterization of the *Escherichia coli* Holo-Acyl Carrier Protein Synthase," *J Biol Chem* 270(42):24658-24661.
Lambalot, R.H. (Nov. 1996). "A New Enzyme Super Family—the Phosphopantetheinyl Transferases," *Chemistry & Biology* 3(11):923-936.
Mofid, M.R. et al. (2002). "Recognition of Hybrid Peptidyl Carrier Proteins/Acyl Carrier Proteins in Nonribosomal Peptide Synthetase Modules by the 4'-Phophopantetheinyl Transferases AcpS and Sfp," *J Biol Chem* 277(19):17023-17031.
Murad, A. et al. (2000). "Clp10, an Efficient and Convenient Integrating Vector for *Candida albicans*," *Yeast* 16:325-327.
Stuible, H-P. et al. (Aug. 28, 1998). "A Novel Phosphopantetheine: Protein Transferase Activiating Yeast Mitochondrial Acyl Carrier Protein," *J Biol Chem* 273(35) 22334-22339.
Turner, G. et al. (Sep. 2006). "Gene Essentiality in *Aspergillus fumigatus*," *Medical Mycology* 44:S87-S90.
Duckworth, B.P. et al. (Aug. 2010, e-published Apr. 9, 2010). "Development of a High-Throughput Fluorescence Polarization Assay for the Discovery of Phosphopantetheinyl Transferase Inhibitors," *Analytical Biochemistry* 403(1-2):13-19.
GenBank Accession No. Q4W9R0, created Jul. 5, 2005, located at <http://www.ncbi.nlm.nih.gov/protein/Q4W9R0>, last visited on Sep. 11, 2014, 1 page.

(Continued)

*Primary Examiner* — Catherine S Hibbert
(74) *Attorney, Agent, or Firm* — Morrison & Foerster LLP

(57) ABSTRACT

A method of identifying an antifungal agent which targets a PPTB protein of a fungus comprising determining whether a candidate compound binds to or inhibits a PPTB protein, wherein binding or inhibition indicates that the candidate substance is an antifungal agent.

12 Claims, 3 Drawing Sheets

(56) References Cited

OTHER PUBLICATIONS

GenBank Accession No. XP_723308.1, located at <http://www.ncbi.nlm.nih.gov/protein/XP_723308.1>, last visited on Sep. 11, 2014, 1 page.

GenBank Accession No. Q4WJA9, created Jul. 5, 2005, located at <http://www.ncbi.nlm.nih.gov/protein/Q4WJA9>, last visited on Sep. 11, 2014, 1 page.

GenBank Accession No. Q5AHH7, created Apr. 26, 2005, located at <http://www.ncbi.nlm.nih.gov/protein/Q5AHH7>, last visited on Sep. 11, 2014, 1 page.

Joshi, A.K. et al. (Aug. 29, 2003, e-published Jun. 18, 2003). "Cloning, Expression, and Characterization of a Human 4'-Phosphopantetheinyl Transferase with Broad Substrate Specificity," *The Journal of Biological Chemistry* 278(35):33142-33149.

Allen, G. et al. (Apr. 2011, e-published Dec. 30, 2010). "Functional Analysis of a Mitochondrial Phosphopantetheinyl Transferase (PPTase) Gene pptB in Aspergillus Fumigatus," *Fungal Genetics and Biology* 48(4):456-464.

Ehmann, D.E. et al. (May 1999). "Lysine Biosynthesis in *Saccharomyces cerevisiae*: Mechanism of Alpha-Aminoadipate Reductase (Lys2) Involves Posttranslational Phosphopantetheinylation by Lys5," *Biochemistry* 38(19):6171-6177.

Fichtlscherer, F. et al. (2000). "A Novel Function of Yeast Fatty Acid Synthase. Subunit alpha is Capable of Self-Pantetheinylation," *Eur. J. Biochem.* 267(9):2666-2671.

Keszenman-Pereyra, D. et al. (Jun. 2003, e-published Mar. 19, 2003). "The npgA/ cfwA Gene Encodes a Putative 4'-Phosphopantetheinyl Transferase Which is Essential for Penicillin Biosynthesis in Aspergillus Nidulans," *Current Genetics* 43(3):186-190.

\* cited by examiner

SEQUENCE LISTING

```
<160> NUMBER OF SEQ ID NOS: 44

<210> SEQ ID NO 1
<211> LENGTH: 20
<212> TYPE: DNA
<213> ORGANISM: Artificial sequence
<220> FEATURE:
<223> OTHER INFORMATION: Primer for PPTB knock-out in Aspergillus
      fumigatus

<400> SEQUENCE: 1
gcgttgatgc agctgtgtat                                               20

<210> SEQ ID NO 2
<211> LENGTH: 20
<212> TYPE: DNA
<213> ORGANISM: Artificial sequence
<220> FEATURE:
<223> OTHER INFORMATION: Primer for PPTB knock-out in Aspergillus
      fumigatus

<400> SEQUENCE: 2
```
tagccgaggc aagtagcagt					20

<210> SEQ ID NO 3
<211> LENGTH: 4915
<212> TYPE: DNA
<213> ORGANISM: Artificial sequence
<220> FEATURE:
<223> OTHER INFORMATION: Plasmid pMB4 zeo

<400> SEQUENCE: 3

| | | | | | |
|---|---|---|---|---|---|
| aattcgcctc | aaacaatgct | cttcaccctc | ttcgcgggtc | tgaaataccc | tcacctggca | 60 |
| acagcaattg | gcgcttcatg | gctgtttttc | cgatctctct | acttgtacgg | ctatgtgtac | 120 |
| tcgggtaagc | cacaaggcaa | gggcagattg | ctgggaggtt | tcttctggtt | ttctcaaggc | 180 |
| gctctgtggg | ctctgagtgt | gtttggtgtt | gccaaagaca | tgatctctta | ctgagagtta | 240 |
| ttctgtgtct | gacgaaatat | gttgtgtata | tatatatatg | tacgttaaaa | gttccgtgga | 300 |
| gttaccagtg | attgaccaat | gttttatctt | ctacagttct | gcctgtctac | cccattctcg | 360 |
| ctgtacctga | ctacagagta | gtttaattgt | ggttgacccc | acagtcggag | gcggaggaat | 420 |
| acagcaccga | tgtggcctgt | ctccatccag | attggcacgc | aattttttaca | cgcggaaaag | 480 |
| atcgagatag | agtacgactt | taaatttagt | ccccggcggc | ttctatttta | gaatatttga | 540 |
| gatttgattc | tcaagcaatt | gatttggttg | ggtcaccctc | aattggataa | tatacctcat | 600 |
| tgctcggcta | cttcaactca | tcaatcaccg | tcataccccg | catataaccc | tccattccca | 660 |
| cgatgtcgtc | caagtcgcaa | ttgacttacg | gtgctcgagc | cagcaagcac | cccaatcctc | 720 |
| tggcaaagag | acttttttgag | attgccgaag | caaagaagac | aaacgttacc | gtctctgctg | 780 |
| atgtgacgac | aacccgagaa | ctcctggacc | tcgctgaccg | tacggaagct | gttggatcca | 840 |
| atacatatgc | cgtctagcaa | tggactaatc | aacttttgat | gatacaggtc | tcggtcccta | 900 |
| catcgccgtc | atcaagacac | acatcgacat | cctcaccgat | ttcagcgtcg | acactatcaa | 960 |
| tggcctgaat | gtgctggctc | aaaagcacaa | ctttttgatc | ttcgaggacc | gcaaattcat | 1020 |
| cgacatcggc | aataccgtcc | agaagcaata | ccacggcggt | gctctgagga | tctccgaatg | 1080 |
| ggcccacatt | atcaactgca | gcgttctccc | tggcgagggc | atcgtcgagg | ctctggccca | 1140 |
| gaccgcatct | gcgcaagact | tcccctatgg | tcctgagaga | ggactgttgg | tcctggcaga | 1200 |
| gatgacctcc | aaaggatcgc | tggctacggg | cgagtatacc | aaggcatcgg | ttgactacgc | 1260 |
| tcgcaaatac | aagaacttcg | ttatgggttt | cgtgtcgacg | cgggccctga | cggaagtgca | 1320 |
| gtcggatgtg | tcttcagcct | cggaggatga | agatttcgtg | gtcttcacga | cgggtgtgaa | 1380 |
| cctctcttcc | aaaggagata | agcttggaca | gcaataccag | actcctgcat | cggctattgg | 1440 |
| acgcggtgcc | gactttatca | tcgccggtcg | aggcatctac | gctgctcccg | acccggttga | 1500 |
| agctgcacag | cggtaccaga | aagaaggctg | ggaagcttat | atggcagag | tatgcggcaa | 1560 |
| gtcatgattt | cctcttggag | caaaagtgta | gtgccagtac | gagtgttgtg | gaggaaggct | 1620 |
| gcatacattg | tgcctgtcat | taaacgatga | gctcgtccgt | attggcccct | gtaatgccat | 1680 |
| gttttccgcc | cccaatcgtc | aaggttttcc | ctttgttaga | ttcctaccag | tcatctagca | 1740 |
| agtgaggtaa | gctttgccag | aaacgccaag | gctttatcta | tgtagtcgat | aagcaaagtg | 1800 |
| gactgatagc | ttaatatgga | aggtccctca | ggacaagtcg | acctgtgcag | aagagataac | 1860 |
| agcttggcat | cacgcatcag | tgcctcctct | cagacagaat | tcgagctcgg | tacccgggga | 1920 |
| tcctctagct | cgagcacgtg | ttgacaatta | atcatcggca | tagtatatcg | gcatagtata | 1980 |
| atacgacaag | gtgaggaact | aaaccatggc | caagttgacc | agtgccgttc | cggtgctcac | 2040 |

```
cgcgcgcgac gtcgccggag cggtcgagtt ctggaccgac cggctcgggt tctcccggga    2100
cttcgtggag gacgacttcg ccggtgtggt ccgggacgca gtgaccctgt tcatcagcgc    2160
ggtccaggac caggtggtgc cggacaacac cctggcctgg gtgtgggtgc gcggcctgga    2220
cgagctgtac gccgagtggt cggaggtcgt gtccacgaac ttccgggacg cctccgggcc    2280
ggccatgacc gagatcggcg agcagccgtg ggggcgggag ttcgccctgc gcgacccggc    2340
cggcaactgc gtgcacttcg tggccgagga gcaggactga gaattcccgg ggatcctcta    2400
gagtcgacct gcaggcatgc aagcttgcca acgactacgc actagccaac aagagcttca    2460
gggttgagat gtgtataaga gacagctgtc ttaatgaatc ggccaacgcg cggggagagg    2520
cggtttgcgt attgggcgct cttccgcttc ctcgctcact gactcgctgc gctcggtcgt    2580
tcggctgcgg cgagcggtat cagctcactc aaaggcggta atacggttat ccacagaatc    2640
aggggataac gcaggaaaga acatgtgagc aaaaggccag caaaaggcca ggaaccgtaa    2700
aaaggccgcg ttgctggcgt ttttccatag gctccgcccc cctgacgagc atcacaaaaa    2760
tcgacgctca agtcagaggt ggcgaaaccc gacaggacta taaagatacc aggcgtttcc    2820
ccctggaagc tccctcgtgc gctctcctgt tccgaccctg ccgcttaccg gatacctgtc    2880
cgcctttctc ccttcgggaa gcgtggcgct ttctcatagc tcacgctgta ggtatctcag    2940
ttcggtgtag gtcgttcgct ccaagctggg ctgtgtgcac gaaccccccg ttcagcccga    3000
ccgctgcgcc ttatccggta actatcgtct tgagtccaac ccggtaagac acgacttatc    3060
gccactggca gcagccactg gtaacaggat tagcagagcg aggtatgtag gcggtgctac    3120
agagttcttg aagtggtggc ctaactacgg ctacactaga aggacagtat ttggtatctg    3180
cgctctgctg aagccagtta ccttcggaaa aagagttggt agctcttgat ccggcaaaca    3240
aaccaccgct ggtagcggtg gtttttttgt ttgcaagcag cagattacgc gcagaaaaaa    3300
aggatctcaa gaagatcctt tgatcttttc tacggggtct gacgctcagt ggaacgaaaa    3360
ctcacgttaa gggattttgg tcatgagatt atcaaaaagg atcttcacct agatcctttt    3420
aaattaaaaa tgaagtttta aatcaatcta agtatatat gagtaaactt ggtctgacag    3480
ttaccaatgc ttaatcagtg aggcacctat ctcagcgatc tgtctatttc gttcatccat    3540
agttgcctga ctccccgtcg tgtagataac tacgatacgg gagggcttac catctggccc    3600
cagtgctgca atgataccgc gagacccacg ctcaccggct ccagatttat cagcaataaa    3660
ccagccagcc ggaagggccg agcgcagaag tggtcctgca actttatccg cctccatcca    3720
gtctattaat tgttgccggg aagctagagt aagtagttcg ccagttaata gtttgcgcaa    3780
cgttgttgcc attgctacag gcatcgtggt gtcacgctcg tcgtttggta tggcttcatt    3840
cagctccggt tcccaacgat caaggcgagt tacatgatcc cccatgttgt gcaaaaaagc    3900
ggttagctcc ttcggtcctc cgatcgttgt cagaagtaag ttggccgcag tgttatcact    3960
catggttatg gcagcactgc ataattctct tactgtcatg ccatccgtaa gatgcttttc    4020
tgtgactggt gagtactcaa ccaagtcatt ctgagaatag tgtatgcggc gaccgagttg    4080
ctcttgcccg gcgtcaatac gggataaatac cgcgccacat agcagaactt taaaagtgct    4140
catcattgga aaacgttctt cggggcgaaa actctcaagg atcttaccgc tgttgagatc    4200
cagttcgatg taacccactc gtgcacccaa ctgatcttca gcatctttta ctttcaccag    4260
cgtttctggg tgagcaaaaa caggaaggca aaatgccgca aaaaagggaa taagggcgac    4320
acggaaatgt tgaatactca tactcttcct ttttcaatat tattgaagca tttatcaggg    4380
```

```
ttattgtctc atgagcggat acatatttga atgtatttag aaaaataaac aaatagggt    4440 tccgcgcaca tttccccgaa aagtgccacc tgacgtctaa gaaaccatta ttatcatgac   4500
attaacctat aaaaataggc gtatcacgag gccctttcgt ctcgcgcgtt tcggtgatga   4560
cggtgaaaac ctctgacaca tgcagctccc ggagacggtc acagcttgtc tgtaagcgga   4620
tgccgggagc agacaagccc gtcagggcgc gtcagcgggt gttggcgggt gtcgggctg    4680 gcttaactat gcggcatcag agcagattgt actgagagtg caccatatgc ggtgtgaaat   4740
accgcacaga tgcgtaagga gaaaataccg catcaggcgc cattcgccat tcaggctgcg   4800
caactgttgg gaagggcgat cggtgcgggc ctcttcgcta ttacgacagc tgtctcttat   4860
acacatctca accatcatcg atgaattttc tcgggtgttc tcgcatattg gctcg        4915
```

<210> SEQ ID NO 4
<211> LENGTH: 20
<212> TYPE: DNA
<213> ORGANISM: Artificial sequence
<220> FEATURE:
<223> OTHER INFORMATION: Primer for checking site of the transposon
      insertion in the PPTB gene

<400> SEQUENCE: 4

```
gttcttggtt tcacctctgc                                                  20
```

<210> SEQ ID NO 5
<211> LENGTH: 23
<212> TYPE: DNA
<213> ORGANISM: Artificial sequence
<220> FEATURE:
<223> OTHER INFORMATION: Primer for checking site of the transposon
      insertion in the PPTB gene

<400> SEQUENCE: 5

```
gagccaatat gcgagaacac ccg                                              23
```

<210> SEQ ID NO 6
<211> LENGTH: 20
<212> TYPE: DNA
<213> ORGANISM: Artificial sequence
<220> FEATURE:
<223> OTHER INFORMATION: Primer for checking site of the transposon
      insertion in the PPTB gene

<400> SEQUENCE: 6

```
cgactacgca ctagccaaca                                                  20
```

<210> SEQ ID NO 7
<211> LENGTH: 462
<212> TYPE: DNA
<213> ORGANISM: Aspergillus fumigatus

<400> SEQUENCE: 7

```
atgaaactaa ttcctttcc atatcccctc aatataggga cggatgtcgt tcatctcccc     60
cgaattctcc gcctcatcaa ccgtcccgac tacttccacc gcttcacccg gcggatcctc   120
cacgaacagg agcagcgaga cttccgcacc agattctccc tcccaccacc atcgtccggc   180
gcagaaaaga ctggactcaa tccaataacg ccagatatgg cgcgctggct ggctggccgt   240
ttcgcggcaa aagaggcagc acgtaaggct gctccggccg gcgcgtcatc cctcgggtgg   300
aaggatgtta ttgttagggt tggtgaggcc gataagggaa gaccggagat tgtgtacttg   360
gatcccatgg gctgtggaga aaccggcgga ggcagagtag gcaagctgtc tatctcgcat   420
```

```
gatgggatt atgtggttgc tacggtgctt gcggctggtt ga                    462
```

```
<210> SEQ ID NO 8
<211> LENGTH: 20
<212> TYPE: DNA
<213> ORGANISM: Artificial sequence
<220> FEATURE:
<223> OTHER INFORMATION: Primer for screening PPTB knock-out
      transformants

<400> SEQUENCE: 8
tcggtgggtt tgatgtaatc                                            20

<210> SEQ ID NO 9
<211> LENGTH: 20
<212> TYPE: DNA
<213> ORGANISM: Artificial sequence
<220> FEATURE:
<223> OTHER INFORMATION: Primer for screening PPTB knock-out
      transformants

<400> SEQUENCE: 9
gacaggcgga gataatgatg                                            20

<210> SEQ ID NO 10
<211> LENGTH: 153
<212> TYPE: PRT
<213> ORGANISM: Apergillus fumigatus

<400> SEQUENCE: 10

Met Lys Leu Ile Pro Phe Pro Tyr Pro Leu Asn Ile Gly Thr Asp Val
1               5                   10                  15

Val His Leu Pro Arg Ile Leu Arg Leu Ile Asn Arg Pro Asp Tyr Phe
            20                  25                  30

His Arg Phe Thr Arg Arg Ile Leu His Glu Gln Glu Gln Arg Asp Phe
        35                  40                  45

Arg Thr Arg Phe Ser Leu Pro Pro Ser Ser Gly Ala Glu Lys Thr
    50                  55                  60

Gly Leu Asn Pro Ile Thr Pro Asp Met Ala Arg Trp Leu Ala Gly Arg
65                  70                  75                  80

Phe Ala Ala Lys Glu Ala Ala Arg Lys Ala Ala Pro Ala Gly Ala Ser
                85                  90                  95

Ser Leu Gly Trp Lys Asp Val Ile Val Arg Val Gly Glu Ala Asp Lys
            100                 105                 110

Gly Arg Pro Glu Ile Val Tyr Leu Asp Pro Met Gly Cys Gly Glu Thr
        115                 120                 125

Gly Gly Gly Arg Val Gly Lys Leu Ser Ile Ser His Asp Gly Asp Tyr
    130                 135                 140

Val Val Ala Thr Val Leu Ala Ala Gly
145                 150

<210> SEQ ID NO 11
<211> LENGTH: 414
<212> TYPE: DNA
<213> ORGANISM: Aspergillus funigatus

<400> SEQUENCE: 11
atgttccgtt ccgctgtcgt ccgctcgttg agagcttccg ttccccgtgc tgtcaggact    60
cctgctgcct tccagatccg tagctctcct gttgctcgtc ctgctcaatt cgcccctcgc   120
tttgcttacc agggtgtccg cctctactct gccccgccg gtctgaacaa ggaggaggtt   180
```

```
gagggccgga tagtcaacct cttgaagaac tttgacaagg tctccgatgc cagcaagatc    240
aacggctctt cccacttctc gaacgacctt ggtctggatt ccctggatac tgttgaggtt    300
gtgatggcta ttgaggagga gttcagcatt gagatccccg acaaggaggc cgacgctatc    360
cacagtgttg acaaggctgt tgagtacatc cttgcccagc tgatgccca ctaa           414

<210> SEQ ID NO 12
<211> LENGTH: 137
<212> TYPE: PRT
<213> ORGANISM: Aspergillus fumigatus

<400> SEQUENCE: 12

Met Phe Arg Ser Ala Val Val Arg Ser Leu Arg Ala Ser Val Pro Arg
1               5                   10                  15

Ala Val Arg Thr Pro Ala Ala Phe Gln Ile Arg Ser Ser Pro Val Ala
            20                  25                  30

Arg Pro Ala Gln Phe Ala Pro Arg Phe Ala Tyr Gln Gly Val Arg Leu
        35                  40                  45

Tyr Ser Ala Pro Ala Gly Leu Asn Lys Glu Glu Val Glu Gly Arg Ile
    50                  55                  60

Val Asn Leu Leu Lys Asn Phe Asp Lys Val Ser Asp Ala Ser Lys Ile
65                  70                  75                  80

Asn Gly Ser Ser His Phe Ser Asn Asp Leu Gly Leu Asp Ser Leu Asp
                85                  90                  95

Thr Val Glu Val Val Met Ala Ile Glu Glu Glu Phe Ser Ile Glu Ile
            100                 105                 110

Pro Asp Lys Glu Ala Asp Ala Ile His Ser Val Asp Lys Ala Val Glu
        115                 120                 125

Tyr Ile Leu Ala Gln Pro Asp Ala His
    130                 135

<210> SEQ ID NO 13
<211> LENGTH: 33
<212> TYPE: DNA
<213> ORGANISM: Artificial sequence
<220> FEATURE:
<223> OTHER INFORMATION: Primer for PCR of Aspergillus fumigatus PPTB

<400> SEQUENCE: 13
gacgacgaca agatgaaact aattccttt cca                                   33

<210> SEQ ID NO 14
<211> LENGTH: 33
<212> TYPE: DNA
<213> ORGANISM: Artificial sequence
<220> FEATURE:
<223> OTHER INFORMATION: Primer for PCR of Aspergillus fumigatus PPTB

<400> SEQUENCE: 14
gaggagaagc ccggttcaac cagccgcaag cac                                  33

<210> SEQ ID NO 15
<211> LENGTH: 30
<212> TYPE: DNA
<213> ORGANISM: Artificial sequence
<220> FEATURE:
<223> OTHER INFORMATION: Primer for PCR of Aspergillus fumigatus ACP

<400> SEQUENCE: 15
gacgacgaca agatgtctgc ccccgccggt                                      30
```

<210> SEQ ID NO 16
<211> LENGTH: 35
<212> TYPE: DNA
<213> ORGANISM: Artificial sequence
<220> FEATURE:
<223> OTHER INFORMATION: Primer for PCR of Aspergillus fumigatus ACP

<400> SEQUENCE: 16
gaggagaagc ccggttagtg ggcatcaggc tgggc                              35

<210> SEQ ID NO 17
<211> LENGTH: 270
<212> TYPE: DNA
<213> ORGANISM: Artificial sequence
<220> FEATURE:
<223> OTHER INFORMATION: ACP sequence generated by PCR

<400> SEQUENCE: 17
atgtctgccc cgccggtct gaacaaggag gaggttgagg ccggatagt caacctcttg      60 aagaactttg acaaggtctc cgatgccagc aagatcaacg gctcttccca cttctcgaac   120
gaccttggtc tggattccct ggatactgtt gaggttgtga tggctattga ggaggagttc   180
agcattgaga tccccgacaa ggaggccgac gctatccaca gtgttgacaa ggctgttgag   240
tacatccttg cccagcctga tgcccactaa                                    270

<210> SEQ ID NO 18
<211> LENGTH: 408
<212> TYPE: DNA
<213> ORGANISM: Candida albicans

<400> SEQUENCE: 18
atgccaaaag taggcactgt attgggtata ggtgttgata tcgtcaattc tgtcagattt    60
gaaagattgt tgacagccaa agcacgtctc ttcggaacaa ggctatccaa gcgaattctt   120
cacccagaac acgaattacc tttgtttcag cagatgcact cacaacgaca agctcaatat   180
cttactggat cttgggcagc aaaggaagca ttattcaaga cattggactt aaactcacag   240
aaagagttca actttaacca atggtaccgc ttccatgatt ccaatgggaa gccatttatt   300
tggaacgatc gatacaaatt gtctgatgaa gagttccatc ttagtatctc acatgatgat   360
tctcttgtaa ttgctacagt acttcgtcag aaggtttatc aaatctaa                408

<210> SEQ ID NO 19
<211> LENGTH: 135
<212> TYPE: PRT
<213> ORGANISM: Candida albicans

<400> SEQUENCE: 19

Met Pro Lys Val Gly Thr Val Leu Gly Ile Gly Val Asp Ile Val Asn
1               5                   10                  15

Ser Val Arg Phe Glu Arg Leu Leu Thr Ala Lys Ser Thr Ser Phe Gly
            20                  25                  30

Thr Arg Leu Ser Lys Arg Ile Leu His Pro Glu His Glu Leu Pro Leu
        35                  40                  45

Phe Gln Gln Met His Ser Gln Arg Gln Ala Gln Tyr Leu Thr Gly Ser
    50                  55                  60

Trp Ala Ala Lys Glu Ala Leu Phe Lys Thr Leu Asp Leu Asn Ser Gln
65                  70                  75                  80

Lys Glu Phe Asn Phe Asn Gln Trp Tyr Arg Phe His Asp Ser Asn Gly
            85                  90                  95

Lys Pro Phe Ile Trp Asn Asp Arg Tyr Lys Leu Ser Asp Glu Glu Phe
        100                 105                 110

His Leu Ser Ile Ser His Asp Asp Ser Leu Val Ile Ala Thr Val Leu
    115                 120                 125

Arg Gln Lys Val Tyr Gln Ile
    130                 135

<210> SEQ ID NO 20
<211> LENGTH: 34
<212> TYPE: DNA
<213> ORGANISM: Artificial sequence
<220> FEATURE:
<223> OTHER INFORMATION: Primer for PCR of Candida albicans PPTB

<400> SEQUENCE: 20
gacgacgaca agatgccaaa agtaggcact gtat                            34

<210> SEQ ID NO 21
<211> LENGTH: 35
<212> TYPE: DNA
<213> ORGANISM: Artificial sequence
<220> FEATURE:
<223> OTHER INFORMATION: Primer for PCR of Candida albicans PPTB

<400> SEQUENCE: 21
gaggagaagc ccggtttaga tttgataaac cttct                           35

<210> SEQ ID NO 22
<211> LENGTH: 333
<212> TYPE: DNA
<213> ORGANISM: Candida albicans

<400> SEQUENCE: 22
atgtttaaat tagctttccg ttccattcgt gcaccagttg ctagagcttc atttgtcaaa    60
ccaattcgtt tttatgttgc cccaccaatt tccaaagatg aagttacttc aagagccatt   120
caagctttga aaaccgttgc tccattacaa gaatccaata tcacattaga atcttctttc   180
caaaaggatt tgggcttaga ttctttagat actgttgaag ctttagtggc attggaagaa   240
gaattcgatt tagaaattcc tgataagatt tctgatgaga taaagactgt tggggaagct   300
gttgattaca tttacaaaga agaatctaaa taa                              333

<210> SEQ ID NO 23
<211> LENGTH: 110
<212> TYPE: PRT
<213> ORGANISM: Candida albicans

<400> SEQUENCE: 23

Met Phe Lys Leu Ala Phe Arg Ser Ile Arg Ala Pro Val Ala Arg Ala
1               5                   10                  15

Ser Phe Val Lys Pro Ile Arg Phe Tyr Val Ala Pro Pro Ile Ser Lys
            20                  25                  30

Asp Glu Val Thr Ser Arg Ala Ile Gln Ala Leu Lys Thr Val Ala Pro
        35                  40                  45

Leu Gln Glu Ser Asn Ile Thr Leu Glu Ser Ser Phe Gln Lys Asp Leu
    50                  55                  60

Gly Leu Asp Ser Leu Asp Thr Val Glu Ala Leu Val Ala Leu Glu Glu
65                  70                  75                  80

Glu Phe Asp Leu Glu Ile Pro Asp Lys Ile Ser Asp Glu Ile Lys Thr
                85                  90                  95

Val Gly Glu Ala Val Asp Tyr Ile Tyr Lys Glu Glu Ser Lys
            100                 105                 110

<210> SEQ ID NO 24
<211> LENGTH: 435
<212> TYPE: DNA
<213> ORGANISM: Candida albicans

<400> SEQUENCE: 24
atgtttagaa ctactttatt aaaatcatta agagcttcag tatcaaaacc ttcaatggtg    60
aaaaccattc aatcatcatc aagatcatta ttcaccatca ccaccatcac taacaacaaa   120
aatgtcactc ctttgacttc atcaatgaac tttattcgtt gttatagtgc cttcccagaa   180
ttaactagag atattgctaa agaaagaatt attgaattat tagaaggtta tgataaagta   240
gatcaatcta aggtgaaat cactgaacaa aactcattta cttctgattt aggtttggat   300
tctttagatg ttgttgaagt gattatggaa ttagaacatg aatttaatat tcaaatccct   360
gataatgaag ccgatagttt aaaaactgtt ggtcaaacta ttgattatat tttagctcaa   420
ccagattctt gttaa                                                    435

<210> SEQ ID NO 25
<211> LENGTH: 144
<212> TYPE: PRT
<213> ORGANISM: Candida albicans

<400> SEQUENCE: 25

Met Phe Arg Thr Thr Leu Leu Lys Ser Leu Arg Ala Ser Val Ser Lys
1               5                   10                  15

Pro Ser Met Val Lys Thr Ile Gln Ser Ser Arg Ser Leu Phe Thr
            20                  25                  30

Ile Thr Thr Ile Thr Asn Asn Lys Asn Val Thr Pro Leu Thr Ser Ser
        35                  40                  45

Met Asn Phe Ile Arg Cys Tyr Ser Ala Phe Pro Glu Leu Thr Arg Asp
    50                  55                  60

Ile Ala Lys Glu Arg Ile Ile Glu Leu Leu Glu Gly Tyr Asp Lys Val
65                  70                  75                  80

Asp Gln Ser Lys Gly Glu Ile Thr Glu Gln Asn Ser Phe Thr Ser Asp
                85                  90                  95

Leu Gly Leu Asp Ser Leu Asp Val Val Glu Val Ile Met Glu Leu Glu
            100                 105                 110

His Glu Phe Asn Ile Gln Ile Pro Asp Asn Glu Ala Asp Ser Leu Lys
        115                 120                 125

Thr Val Gly Gln Thr Ile Asp Tyr Ile Leu Ala Gln Pro Asp Ser Cys
    130                 135                 140

<210> SEQ ID NO 26
<211> LENGTH: 32
<212> TYPE: DNA
<213> ORGANISM: Artificial sequence
<220> FEATURE:
<223> OTHER INFORMATION: Primer for PCR of Candida albicans ACPg

<400> SEQUENCE: 26
gacgacgaca agatggttgc cccaccaatt tc                                  32

<210> SEQ ID NO 27

```
<211> LENGTH: 35
<212> TYPE: DNA
<213> ORGANISM: Artificial sequence
<220> FEATURE:
<223> OTHER INFORMATION: Primer for PCR of Candida albicans ACPg

<400> SEQUENCE: 27
gaggagaagc ccggtttatt tagattcttc tttgt                              35

<210> SEQ ID NO 28
<211> LENGTH: 32
<212> TYPE: DNA
<213> ORGANISM: Artificial sequence
<220> FEATURE:
<223> OTHER INFORMATION: Primer for PCR of Candida albicans ACPe

<400> SEQUENCE: 28
gacgacgaca agatgagtgc cttcccagaa tt                                 32

<210> SEQ ID NO 29
<211> LENGTH: 35
<212> TYPE: DNA
<213> ORGANISM: Artificial sequence
<220> FEATURE:
<223> OTHER INFORMATION: Primer for PCR of Candida albicans ACPe

<400> SEQUENCE: 29
gaggagaagc ccggtttaac aagaatctgg ttgag                              35

<210> SEQ ID NO 30
<211> LENGTH: 20
<212> TYPE: DNA
<213> ORGANISM: Artificial sequence
<220> FEATURE:
<223> OTHER INFORMATION: Primer for PCR of 5' region of Candida albicans
      PPTB gene

<400> SEQUENCE: 30
cacggtttca ccagtgtctg                                               20

<210> SEQ ID NO 31
<211> LENGTH: 45
<212> TYPE: DNA
<213> ORGANISM: Artificial sequence
<220> FEATURE:
<223> OTHER INFORMATION: Primer for PCR of 5' region of Candida albicans
      PPTB gene

<400> SEQUENCE: 31
gatctaggct tggccaagtc ggccgctgga aaaatttccc cgaga                   45

<210> SEQ ID NO 32
<211> LENGTH: 25
<212> TYPE: DNA
<213> ORGANISM: Artificial sequence
<220> FEATURE:
<223> OTHER INFORMATION: Primer for preparation of URA3-MET3 construct

<400> SEQUENCE: 32
cggccgactt ggccaagcct agatc                                         25

<210> SEQ ID NO 33
<211> LENGTH: 25
<212> TYPE: DNA
<213> ORGANISM: Artificial sequence
<220> FEATURE:
<223> OTHER INFORMATION: Primer for preparation of URA3-MET3 construct
```

<400> SEQUENCE: 33
tggggagggt atttactttt aaata                                        25

<210> SEQ ID NO 34
<211> LENGTH: 45
<212> TYPE: DNA
<213> ORGANISM: Artificial sequence
<220> FEATURE:
<223> OTHER INFORMATION: Primer for amplifying first 394 bp of Candida
      alibicans PPTB coding sequence

<400> SEQUENCE: 34
tatttaaaag taaataccct ccccaatgcc aaaagtaggc actgt                   45

<210> SEQ ID NO 35
<211> LENGTH: 24
<212> TYPE: DNA
<213> ORGANISM: Artificial sequence
<220> FEATURE:
<223> OTHER INFORMATION: Primer for amplifying first 394 bp of Candida
      albicans PPTB coding sequence

<400> SEQUENCE: 35
ccttctgacg aagtactgta gcaa                                         24

<210> SEQ ID NO 36
<211> LENGTH: 120
<212> TYPE: DNA
<213> ORGANISM: Artificial sequence
<220> FEATURE:
<223> OTHER INFORMATION: Primers for the PPTB knock-out in Candida
      albicans

<400> SEQUENCE: 36
ggaaattttt ccagcatcga gttagtagct ctctgtacct taatatctac tacatgtgat   60
gccaaaagta ggcactgtat tgggtatagg tgttgatatc ccagggtttt cccagtcacg  120

<210> SEQ ID NO 37
<211> LENGTH: 118
<212> TYPE: DNA
<213> ORGANISM: Artificial sequence
<220> FEATURE:
<223> OTHER INFORMATION: Primer for PPTB knock-out in Candida albicans

<400> SEQUENCE: 37
ctttagattt gataaacctt ctgacgaagt actgtagcaa ttacaagaga atcatcatgt   60
gagatactaa gatggaactc ttcatcagac aatttgtatc actaaaggga acaaaagc   118

<210> SEQ ID NO 38
<211> LENGTH: 20
<212> TYPE: DNA
<213> ORGANISM: Artificial sequence
<220> FEATURE:
<223> OTHER INFORMATION: Primer for screening PPTB knock-out
      transformants

<400> SEQUENCE: 38
gctgttccca agtttggtgt                                              20

<210> SEQ ID NO 39
<211> LENGTH: 20
<212> TYPE: DNA
<213> ORGANISM: Artificial sequence
<220> FEATURE:

```
<223> OTHER INFORMATION: Primer for screening PPTB knock-out
      transformants

<400> SEQUENCE: 39
tgctactggt gaggcatgag                                                20

<210> SEQ ID NO 40
<211> LENGTH: 20
<212> TYPE: DNA
<213> ORGANISM: Artificial sequence
<220> FEATURE:
<223> OTHER INFORMATION: Primer for screening PPTB knock-out
      transformants

<400> SEQUENCE: 40
caagacccat cacaatgtcg                                                20

<210> SEQ ID NO 41
<211> LENGTH: 19
<212> TYPE: DNA
<213> ORGANISM: Artificial sequence
<220> FEATURE:
<223> OTHER INFORMATION: Primer for screening PPTB knock-out
      transformants

<400> SEQUENCE: 41
attgctgtgg atcacgtgc                                                 19

<210> SEQ ID NO 42
<211> LENGTH: 20
<212> TYPE: DNA
<213> ORGANISM: Artificial sequence
<220> FEATURE:
<223> OTHER INFORMATION: Primer for screening PPTB knock-out
      transformants

<400> SEQUENCE: 42
gctgttccca agtttggtgt                                                20

<210> SEQ ID NO 43
<211> LENGTH: 20
<212> TYPE: DNA
<213> ORGANISM: Artificial sequence
<220> FEATURE:
<223> OTHER INFORMATION: Primer for screening PPTB knock-out
      transformants

<400> SEQUENCE: 43
gcccatctaa taggttgagc                                                20

<210> SEQ ID NO 44
<211> LENGTH: 20
<212> TYPE: DNA
<213> ORGANISM: Artificial sequence
<220> FEATURE:
<223> OTHER INFORMATION: Primer for screening PPTB knock-out
      transformants

<400> SEQUENCE: 44
gcaattcttg aacgagcaca                                                20
```

ANTIFUNGAL TARGET

CROSS REFERENCE TO RELATED APPLICATIONS

This application is a National Phase application under 35 U.S.C. §371 of International Application No. PCT/GB2010/001091, having an International Filing Date of Jun. 4, 2010, which claims priority to British Application No. GB 0909743.7 filed on Jun. 5, 2009, each of which are incorporated herein by reference in their entireties.

The present invention relates to fungal phosphopantetheinyl transferase B proteins (PPTBs) and their use as antifungal targets, to screening methods for PPTB inhibitors and their use as antifungal compounds, and to pharmaceutical compositions containing them and their use in medicine, specifically in the treatment of an individual susceptible to or suffering from an antifungal infection. In particular the compounds find use in the treatment of systemic or topical fungal infections, e.g. caused by fungi of *Aspergillus* and *Candida* species.

BACKGROUND OF THE INVENTION

Phosphopantetheinyl transferases (PPTs) modify their substrate proteins by the addition of a phosphopantetheinyl group derived from coenzyme A. Three PPTs are present in *S. cerevisiae*: LYS5 (PPTA) is required for the activation of alpha-aminoadipate reductase (an enzyme of the lysine biosynthesis pathway), as well as being important for siderophore and polyketide synthesis; PPT2 (PPTB) pantetheinylates mitochondrial acyl carrier protein (ACP), which is involved in mitochondrial fatty acid biosynthesis; and FAS2 fatty acid synthase alpha subunit, which is a multi-domain protein with a PPT function involved in cytoplasmic fatty acid synthesis. These PPTs are also found in other fungi, such as *Aspergillus fumigatus* and *Candida albicans*, and homologues of PPTA and PPTB are found in bacteria, with PPTAs resembling the surfactin synthetase-activating enzyme (sfp) family of bacterial proteins, and PPTBs resembling the bacterial acyl-carrier protein synthases. PPTA, but not PPTB, is found in animals.

SUMMARY OF INVENTION

Based on the characterisation of PPTB and the development of a screening method that is able to detect inhibitors of PPTB, the inventors have elucidated a new way of obtaining antifungal drugs. One aspect of the invention concerns the finding that PPTB is essential in fungi. It is also an object of the present invention to provide methods for assaying fungal PPTB in vitro suitable for high-throughput screening. The invention also provides methods for screening for inhibitors of fungal PPTB.

Additionally, the inventors have found that fungi, e.g. *C. albicans*, may have two ACP molecules, only one of which is suitable as a substrate for PPTB. Furthermore, the inventors have identified assay conditions that lead to reaction products which are surprisingly stable and enable samples to be read for at least five days after the assay is carried out, so that large numbers of samples can be processed.

Accordingly the invention provides the following:
a method of identifying an antifungal agent comprising determining whether a candidate compound binds to or inhibits:
  (i) a PPTB protein which comprises the sequence shown by SEQ ID NO:10 or SEQ ID No. 19,
  (ii) a PPTB protein which is a homologue of (i),
  (iii) a protein which has at least 50% identity with (i) or (ii),
  (iv) a protein comprising a variant or a fragment of (i), (ii) or (iii) which fragment has a length of at least 50 amino acids,
  wherein binding or inhibition of (i), (ii), (iii) or (iv) indicates that the candidate substance is an antifungal agent,
use of the method to identify or obtain an antifungal agent,
a compound identified by the method which impairs fungal PPTB function for use as an antifungal compound,
use of an antifungal agent identified by the method in the manufacture of a medicament for prevention or treatment of fungal infection,
a method for preventing or treating a fungal infection comprising administering an antifungal agent identified by the screening method of the invention,
a pharmaceutical composition comprising a PPTB inhibitor and a pharmaceutically acceptable carrier.

DESCRIPTION OF THE SEQUENCES

SEQ ID Nos. 1 and 2; Primers for PPTB knock out in *A. fumigatus*
SEQ ID Nos. 3; Plasmid pMB4 zeo
SEQ ID Nos. 4-6; Primers for checking the site of transposon insertion in the PPTB gene
SEQ ID No. 7; *A. fumigatus* PPTB coding sequence
SEQ ID Nos. 8 and 9; Primers for screening PPTB knockout transformants
SEQ ID No. 10; *A. fumigatus* PPTB protein sequence
SEQ ID No. 11; *A. fumigatus* ACP coding sequence
SEQ ID No. 12; *A. fumigatus* ACP protein sequence
SEQ ID Nos. 13 and 14; Primers for PCR of *A. fumigatus* PPTB
SEQ ID Nos. 15 and 16; Primers for PCR of *A. fumigatus* ACP
SEQ ID No. 17; ACP sequence generated by PCR
SEQ ID No. 18; *C. albicans* PPTB coding sequence
SEQ ID Ns. 19; *C. albicans* PPTB protein sequence
SEQ ID Nos. 20 and 21; Primers for PCR of *C. albicans* PPTB
SEQ ID Nos. 22; *C. albicans* ACPg coding sequence
SEQ ID Nos. 23; *C. albicans* ACPg protein sequence
SEQ ID Nos. 24; *C. albicans* ACPe coding sequence
SEQ ID Nos. 25; *C. albicans* ACPe protein sequence
SEQ ID Nos. 26 and 27; Primers for PCR of *C. albicans* ACPg
SEQ ID Nos. 28 and 29; Primers for PCR of *C. albicans* ACPe
SEQ ID Nos. 30 and 31; Primers for PCR of 5' region of *C. albicans* PPTB gene;
SEQ ID Nos. 32 and 33; Primers for preparation of URA3-MET3 construct;
SEQ ID Nos. 34 and 35; Primers for amplifying first 394 bp of *C. albicans* PPTB coding sequence;
SEQ ID Nos. 36 and 37; Primers for PPTB knock out in *C. albicans*
SEQ ID Nos. 38 and 39; Primers for screening PPTB knockout transformants;
SEQ ID Nos. 40 and 41: Primers for screening PPTB knockout transformants;
SEQ ID Nos. 42 and 43: Primers for screening PPTB knockout transformants;
SEQ ID Nos. 44; Primer for screening PPTB knockout transformants

DETAILED DESCRIPTION OF THE INVENTION

As mentioned above the invention relates to use of particular protein sequences (termed "proteins of the invention" herein) which are of, or derived from, fungal PPTB and ACP proteins (including homologues and/or fragments of the fungal PPTB and ACP proteins) to identify antifungal agents. The methods of the invention provide assays to screen compounds as potential antifungal agents.

Proteins of the Invention

As used herein, a PPTB protein (phosphopantetheinyl transferase B) may be defined as an enzyme which is capable of catalysing transferring a 4'-phosphopantetheine group from coenzyme A to acyl carrier protein (ACP). The PPTBs of the invention generally fall within classification EC 2.7.8.—of the enzyme commission.

As used herein, the term essential fungal gene may be defined as one which, when disrupted genetically (for example when not expressed) in a fungus, prevents survival or significantly retards growth of the cell on minimal or defined medium, or in guinea pigs, mice, rabbits or rats infected with the fungus.

As used herein, the term antifungal agent may be defined as an agent that retards, destroys or prevents the growth of fungi, an agent used to treat fungal infections, or an agent that selectively eliminates fungal pathogens from a host with minimal toxicity to the host. The antifungal efficacy of a compound may be measured in vitro, e.g. with cultures of fungi, or in vivo, e.g. in an infected host.

A protein of the invention (or a fungal PPTB protein or ACP) may be defined by similarity in sequence to another member of the family. As mentioned above this similarity may be based on percentage identity (for example to sequences SEQ ID No. 10, 12, 19 or 23). Alternatively, a PPTB protein may be defined as a protein which is identified as a member of the PFAM 4'-phosphopantetheine transferase superfamily; an ACP may be defined as a protein with matches to the Interpro profiles IPR003231, IPR006162, IPR006163 or IPR009081.

The protein of the invention may be in isolated form (such as non-cellular form), for example when used in the method of the invention. Preferably, the isolated protein comprises a PPTB or an ACP. The protein may comprise native, synthetic or recombinant protein. The protein may comprise combinations of native, synthetic or recombinant protein. The proteins of the invention may have a sequence which is the same as, or different from, naturally occurring PPTB or ACP proteins. The protein sequences may be synthesised de novo, or may be native amino acid/protein sequence, or a derivative thereof.

It is to be understood that the term "isolated from" may be read as "of" herein. Therefore references to proteins being "isolated from" a particular organism include proteins which were prepared by means other than obtaining them from the organism, such as synthetically or recombinantly.

Preferably, the protein, is isolated from a fungus, more preferably a filamentous fungus, even more preferably an Ascomycete.

Preferably, the protein of the invention is isolated from an organism independently selected from the genera *Absidia; Acremonium; Alternaria; Aspergillus; Bipolaris; Blastomyces; Blumeria; Candida; Cladosporium; Coccidioides; Colletotrichium; Cryptococcus; Curvularia; Encephalitozoon; Epicoccum; Epidermophyton; Exophiala; Exserohilum; Fonsecaea; Fusarium; Histoplasma; Leptosphaeria; Microsporum; Mycosphaerella; Neurospora; Paecilomyces; Paracoccidioides; Penicillium; Phialophora; Phytophthora; Plasmopara; Pneumocystis; Pseudallescheria; Pyricularia; Pythium; Puccinia; Rhizoctonia; Rhizomucor; Rhizopus; Saccharomyces; Scedosporium; Scopulariopsis; Sporothrix; Trichophyton; Trichosporon; Ustilago* and *Wangiella.*

Preferably, the protein of the invention is isolated from an organism selected from the species *Absidia corymbifera; Acremonium* spp.: *Alternaria alternata; Aspergillus flavus; Aspergillus fumigatus; Aspergillus nidulans; Aspergillus niger; Aspergillus parasiticus; Aspergillus terreus; Bipolaris* spp.; *Blastomyces dermatitidis; Blumeria graminis; Candida albicans; Candida glabrata; Candida krusei; Candida parapsilosis; Candida tropicalis; Cladosporium carrionii; Cladosporium cladosporoides; Cladosporium herbarium; Coccidioides immitis; Coccidioides posadasii; Curvularia lunata; Colletotrichium trifolii; Cryptococcus neoformans; Encephalitozoon cuniculi; Epicoccum nigrum; Epidermophyton floccosum; Exophiala* spp.; *Exserohilum rostratum; Fonsecaea pedrosoi; Fusarium graminarium; Fusarium solani; Fusarium sporotrichoides; Histoplasma capsulatum; Leptosphaeria nodorum; Microsporum canis; Mycosphaerella graminicola; Paecilomyces lilanicus; Paecilomyces varioti; Paracoccidioides brasiliensis; Penicillium chlysogenum; Phialophora verrucosa; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Rhizomucor* spp.: *Rhizopus* spp.; *Saccharomyces* spp.; *Scedosporium apiospermum; Scedosporium prolificans; Scopulariopsis brevicaulis; Sporothrix* spp.; *Trichophyton mentagrophytes; Trichophyton interdigitale; Trichophyton rubrum; Trichosporon asahii; Trichosporon beigelii* and *Ustilago maydis.*

Preferably, the protein is isolated from an organism from the genus *Aspergillus* or *Candida.*

Preferably, the protein, is isolated from an organism of the species *Aspergillus fumigatus* or *Candida albicans.*

Variants of the above mentioned proteins are also provided, and are discussed below.

In one embodiment, the protein of the invention comprises an amino acid sequence substantially similar to that set out in SEQ ID Nos 10, 12, 19 or 23, or variants thereof.

By the term "native amino acid/protein" is meant an amino acid or protein produced naturally from biological sources either in vivo or in vitro.

By the term "synthetic amino acid/protein" is meant an amino acid or protein which has been produced artificially or de novo using a protein synthesis machine known in the art.

By the term "recombinant amino acid/protein" is meant an amino acid or protein which has been produced using recombinant DNA or protein technology or methodologies which are known to the skilled technician.

By the term "homologue" is meant a protein with similar or identical function due to a shared ancestry. For example, the PPTB proteins of *A. fumigatus* and *C. albicans*, which are assumed to share a common fungal ancestor, are said to be homologous. Homologous proteins can be compared by calculating the percentage identity at the sequence level.

The term "variant", and the terms "substantially similar" are used herein to refer to related sequences. As discussed below such related sequences are typically homologous to (share percentage identity with) a given sequence, for example over the entire length of the sequence or over a portion of a given length. The related sequence may also be a fragment of the sequence or of a homologous sequence. A variant protein may be encoded by a variant polynucleotide.

By the term "variant", and the terms "substantially similar", we mean that the sequence has at least 30%, preferably 40%, more preferably 50%, and even more preferably, 60% sequence identity with the amino acid/protein sequences of any one of the sequences referred to. An amino acid/protein sequence with a greater identity than 65% to any of the sequences referred to is also envisaged. An amino acid/protein sequence with a greater identity than 70% to any of the sequences referred to is also envisaged. An amino acid/protein sequence with a greater identity than 75% to any of the sequences referred to is also envisaged. An amino acid/protein sequence with a greater identity than 80% to any of the sequences referred to is also envisaged. Preferably, the amino acid/protein sequence has 85% identity with any of the sequences referred to, more preferably 90% identity, even more preferably 92% identity, even more preferably 95% identity, even more preferably 97% identity, even more preferably 98% identity and, most preferably, 99% identity with any of the referred to sequences. A sequence which is "substantially similar" may be the same as the relevant sequence.

The above mentioned percentage identities may be measured over the entire length of the original sequence or over a region of 15, 20, 50 or 100 amino acids of the original sequence. In a preferred embodiment percentage identity is measured with reference to SEQ ID Nos. 10, 12, 19 or 23. Preferably the variant protein has at least 40% identity, such as at least 60%, or at least 80% identity, or at least 90% with SEQ ID Nos. 10, 12, 19 or 23 or a portion of SEQ ID Nos. 10, 12, 19 or 23.

The percentage identity is calculated from an alignment as (N/T)*100, where N is the number of positions at which two sequences share an identical residue, and T is the total number of positions compared. Alternatively, percentage identity can be calculated as (N/S)*100 where S is the length of the shorter sequence being compared.

Alternatively, a substantially similar protein may differ by at least 1, but less than 5, 10, 20, 50 or 100 amino acids from the sequences shown in SEQ ID Nos. 10, 12, 19 or 23. Such differences may each be additions, deletions or substitutions.

The term "variant", and the terms "substantially similar" also include a fragment of the relevant amino acid/protein sequences, including a fragment of the homologous sequences (which have percentage identity to a specified sequence) referred to above. An amino acid/protein fragment will typically comprise at least 10 amino acids, such as at least 15, 20, 25, 30, 35, 40, 50, 80, 100, 150, 200, 300, 400 or 500 amino acids. The fragments may lack at least 3 amino acids, such as at least 5, 7, 10, 15, 20, 30, 40, 50, 60, 70, 80, 90, 100 or 110 amino acids from either or both ends of the protein.

Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. Certain organisms, including *Candida* are known to use non-standard codons compared to those used in the majority of eukaryotes. Any comparisons of polynucleotides and proteins from such organisms with the sequences given here should take these differences into account.

Other modifications in protein sequences are also envisaged and within the scope of the claimed invention, i.e. those which occur during or after translation, e.g. by acetylation, amidation, carboxylation, phosphorylation, proteolytic cleavage or linkage to a ligand.

A protein of the invention may be modified prior to use, preferably to produce a derivative or variant thereof. The protein may be derivatised. The protein may be modified by epitope tagging, addition of fusion partners or purification tags such as glutathione S-transferase, NUS tag, multiple histidines or maltose binding protein, addition of green fluorescent protein, covalent attachment of molecules including biotin or fluorescent tags, chromophores, incorporation of selenomethionine, inclusion or attachment of radioisotopes or fluorescent/non-fluorescent lanthanide chelates, or by addition of sequence encoding the above tags, proteins or epitopes.

The protein of the invention may be used as a fusion protein, which is defined as a PPTB or ACP polypeptide or fragment thereof fused via a covalent bond (e.g. a peptide bond), at optionally the N-terminus or the C-terminus, to an amino acid sequence of another protein (or portion thereof; preferably at least a 10, 20 or 50 amino acid portion of the protein).

Methods of Screening

The invention provides a method of screening which may be used to identify modulators of PPTB proteins, such as inhibitors of activity of the PPTB proteins of the invention. In one embodiment of the method a candidate substance is contacted with a PPTB protein of the invention and whether or not the candidate substance binds or modulates the protein is determined.

The modulator may promote (agonise) or inhibit (antagonise) the activity of the protein. A therapeutic modulator (against fungal infection) will inhibit the activity of a protein of the invention.

Any suitable binding or activity assay may be used. Methods which determine whether a candidate substance is able to bind the protein may comprise providing the protein to a candidate substance and determining whether binding occurs, for example by measuring the amount of the candidate substance which binds the protein. The binding may be determined by measuring a characteristic of the protein that changes upon binding, such as spectroscopic changes. The binding may be determined by measuring reaction substrate or product levels in the presence and absence of the candidate and comparing the levels. The binding may be measured by allowing the transfer of a label from a substrate of the reaction and/or onto a product of the reaction in the presence and absence of the candidate. The label may be a radioisotope, fluorophore, chromophore or enzyme.

The method may be a competitive binding method. This determines whether the candidate is able to inhibit the binding of the protein to an agent which is known to bind to the protein, such as an antibody specific for the protein, or a substrate of the protein.

Whether or not a candidate substance modulates the activity of the protein may be determined by providing the candidate substance to the protein under conditions that permit activity of the protein, and determining whether the candidate substance is able to modulate the activity of the product.

The activity which is measured may be any of the activities of the PPTB protein of the invention mentioned herein, such as phosphopantetheine transferase activity. In one embodiment the screening method comprises carrying out a phosphopantetheine transferase reaction in the presence and absence of the candidate substance to determine whether the candidate substance inhibits the transferase activity of the protein of the invention, wherein the transferase reaction is carried out by contacting said protein with an ACP and coenzyme A, under conditions in which in the absence of the candidate substance the protein catalyses pantetheinylation of the ACP.

In a preferred embodiment the inhibition of the phosphopantetheine transferase reaction is measured by detecting the amount of phosphopantetheine transferred to the ACP, for example by using fluorescently-labelled coenzyme A and measuring the generation of fluorescent ACP. This can be measured using Fluorescence Polarisation. In a further preferred embodiment of the invention, the ACP is labelled with Bodipy-TMR, though other fluorophores can be used.

Alternatively, transfer of the pantetheinyl group can be measured by Fluorescence Resonance Energy Transfer (FRET) using labelled coenzyme A and labelled ACP.

Suitable candidate substances which can tested in the above methods include combinatorial libraries, defined chemical identities, peptide and peptide mimetics, oligonucleotides and natural product libraries, such as display libraries (e.g. phage display libraries). The candidate substances may be chemical compounds. Batches of the candidate substances may be used in an initial screen of, for example, ten substances per reaction, and the substances from batches which show inhibition tested individually. Antibody products (for example, monoclonal and polyclonal antibodies, single chain antibodies, chimeric antibodies and CDR-grafted antibodies) may also be tested.

The inventors have identified conditions such that the assay products are surprisingly stable, enabling microwell plates to be read up to at least five days after the assay was carried out. Therefore in one embodiment of the invention, the assay is carried out under the conditions of, optionally, 50 mM Bis-Tris, and/or 10 mM $MgCl_2$, and/or at pH 6.75, and/or 1% v/v DMSO, and/or at a PPTB enzyme concentration such that the enzyme activity is in a linear range with respect to time and protein concentration, and/or incubated for 20-40 minutes, and/or incubated at room temperature, and/or where the stop reagent is 60 mM EDTA pH8.0, and/or where the assay has a Z' value of ≥0.70, and/or where the assay has a % $CV_{100\%}$ value of ≤4%, and/or where the assay has a W value of >15.

In another embodiment of the invention, the assay is carried out under the conditions of, optionally, between 10 mM and 500 mM Bis-Tris, preferably between 20 mM and 200 mM Bis-Tris, more preferably between 35 mM and 100 mM Bis-Tris, most preferably 50 mM Bis-Tris; and/or between 1 and 50 mM $MgCl_2$, preferably between 2 and 20 mM $MgCl_2$, more preferably between 5 and 15 mM $MgCl_2$, most preferably 10 mM $MgCl_2$; and/or at between pH 4 and pH 9, preferably at between pH5 and pH 8, more preferably at between pH 6 and pH 7, most preferably at pH 6.75; and/or with between 0% and 10% DMSO, preferably between 0.1% and 5% DMSO, more preferably between 0.5% and 2% DMSO, most preferably 1% v/v DMSO; and/or at a PPTB enzyme concentration such that the enzyme activity is in a linear range with respect to time and protein concentration; and/or incubated for between 2 minutes and 5 hours, preferably between 10 minutes and 2.5 hours, more preferably between 15 minutes and 1 hour, most preferable between 20-40 minutes; and/or incubated at between 5° C. and 37° C., preferably between 10° C. and 25° C., more preferably between 15° C. and 20° C., most preferably at room temperature; and/or where the stop reagent is EDTA at a concentration of between 10 and 500 mM and a pH of between 5.0 and 10.0, preferably at a concentration of between 20 and 250 mM and a pH of between 6.0 and 9.0, more preferably at a concentration of between 40 and 100 mM and a pH of between 7.0 and 9.0, most preferably 60 mM EDTA pH8.0; and/or where the assay has a Z' value of ≥0.50, preferably ≥0.60, more preferably ≥0.65, most preferably ≥0.70; and/or where the assay has a % $CV_{100\%}$ value of ≤10%, preferably ≤7%, more preferably ≤5%, most preferably ≤4%; and/or where the assay has a W value of >8, preferably >10, more preferably >12, most preferably >15.

In a further embodiment of the invention, the ACP-Bodipy TMR reaction product is stable for at least up to 5 days such that after 5 days Z'≥0.70, % $CV_{100\%}$≤4% and W>15.

In another embodiment of the invention, the ACP-Bodipy TMR reaction product is stable for at least up to 2, preferably 3, more preferably 4, most preferably 5 days such that after this time the assay has a Z' value of ≥0.50, preferably ≥0.60, more preferably ≥0.65, most preferably ≥0.70; and/or where the assay has a % $CV_{100\%}$ value of ≤10%, preferably ≤7%, more preferably ≤5%, most preferably ≤4%; and/or where the assay has a W value of >8, preferably >10, more preferably >12, most preferably >15.

Treatment of Fungal Infections.

According to a further aspect of the present invention, there is provided use of a protein of the invention for the preparation of a medicament for the treatment of a fungal infection.

Preferably, the medicament is adapted to retard or prevent a fungal infection. The fungal infection may be in human, animal or plant. The protein may be used for the development of a drug. The treatment may comprise retarding or preventing fungal infection. Preferably, the drug and/or medicament comprises an inhibitor, preferably a PPTB inhibitor. Preferably, the drug or medicament is adapted to inhibit a the function of the protein or a fragment thereof.

Preferably, the fungal infection comprises an infection by a fungus, more preferably an Ascomycete, and even more preferably, an organism selected from the genera *Absidia; Acremonium; Alternaria; Aspergillus; Bipolaris; Blastomyces; Blumeria; Candida; Cladosporium; Coccidioides; Colletotrichium; Cryptococcus; Curvularia; Encephalitozoon; Epicoccum; Epidermophyton; Exophiala; Exserohilum; Fonsecaea; Fusarium; Histoplasma; Leptosphaeria; Microsporum; Mycosphaerella; Neurospora; Paecilomyces; Paracoccidioides; Penicillium; Phialophora; Phytophthora; Plasmopara; Pneumocystis; Pseudallescheria; Pyricularia; Pythium; Puccinia; Rhizoctonia; Rhizomucor; Rhizopus; Saccharomyces; Scedosporium; Scopulariopsis; Sporothrix; Trichophyton; Trichosporon; Ustilago* and *Wangiella.*

Preferably, the fungal infection comprises an infection by a fungus from the genus *Aspergillus* or *Candida.*

Preferably, the fungal infection comprises an infection by an organism selected from the species *Absidia corymbifera; Acremonium* spp.; *Alternaria alternata; Aspergillus flavus; Aspergillus fumigatus; Aspergillus nidulans; Aspergillus niger; Aspergillus parasiticus; Aspergillus terreus; Bipolaris* spp.; *Blastomyces dermatitidis; Blumeria graminis; Candida albicans; Candida glabrata; Candida krusei; Candida parapsilosis; Candida tropicalis; Cladosporium carri-* onii; *Cladosporium cladosporoides; Cladosporium herbarium; Coccidioides immitis; Coccidioides posadasii; Curvularia lunata; Colletotrichium trifolii; Cryptococcus neoformans; Encephalitozoon cuniculi; Epicoccum nigrum; Epidermophyton floccosum; Exophiala* spp.; *Exserohilum rostratum; Fonsecaea pedrosoi; Fusarium graminarium; Fusarium solani; Fusarium sporotrichoides; Histoplasma capsulatum; Leptosphaeria nodorum; Microsporum canis; Mycosphaerella graminicola; Paecilomyces lilanicus; Paecilomyces varioti; Paracoccidioides brasiliensis; Penicillium chrysogenum; Phialophora verrucosa; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Rhizomucor* spp.; *Rhizopus* spp.; *Saccharomyces* spp.; *Scedosporium apiospermum; Scedosporium prolificans; Scopulariopsis brevicaulis; Sporothrix* spp.; *Trichophyton mentagrophytes; Trichophyton interdigitale; Trichophyton rubrum; Trichosporon asahii; Trichosporon beigelii* and *Ustilago maydis.*

Preferably, the fungal infection comprises an infection by an organism selected from the species *Aspergillus fumigatus* or *Candida albicans.*

Pharmaceutical Compositions

In order to use PPTB inhibitors in therapy (human or veterinary), they will normally be formulated into a pharmaceutical composition in accordance with standard pharmaceutical practice, e.g. by admixing the PPTB inhibitor and a pharmaceutically acceptable carrier.

Thus according to a further aspect of the invention there is provided a pharmaceutical composition comprising a PPTB inhibitor and a pharmaceutically acceptable carrier. The pharmaceutical compositions are particularly useful in the prevention or treatment of fungal infections, preferably, in the treatment of *Aspergillus* or *Candida* fungal infections.

PPTB inhibitors may be administered to a host by any of the routes conventionally used for drug administration, for example they may be administered parenterally, orally, topically (including buccal, sublingual or transdermal) or by inhalation. The most suitable route for administration in any given case will depend on the particular PPTB inhibitor, the infectious organism involved, the host, and the nature and severity of the disease and the physical condition of the host.

The PPTB inhibitor may be administered in combination, e.g. simultaneously, sequentially or separately, with one or more other therapeutically active, e.g. antifungal, compounds.

All publications, including but not limited to patents and patent applications, cited in this specification are herein incorporated by reference as if each individual publication were specifically and individually indicated to be incorporated by reference herein as though fully set forth.

The following examples are to be construed as merely illustrative and not a limitation on the scope of the invention in any way.

Embodiments of the invention will now be described by way of example, with reference to the accompanying drawings in which:—

EXAMPLES

Figure 1:
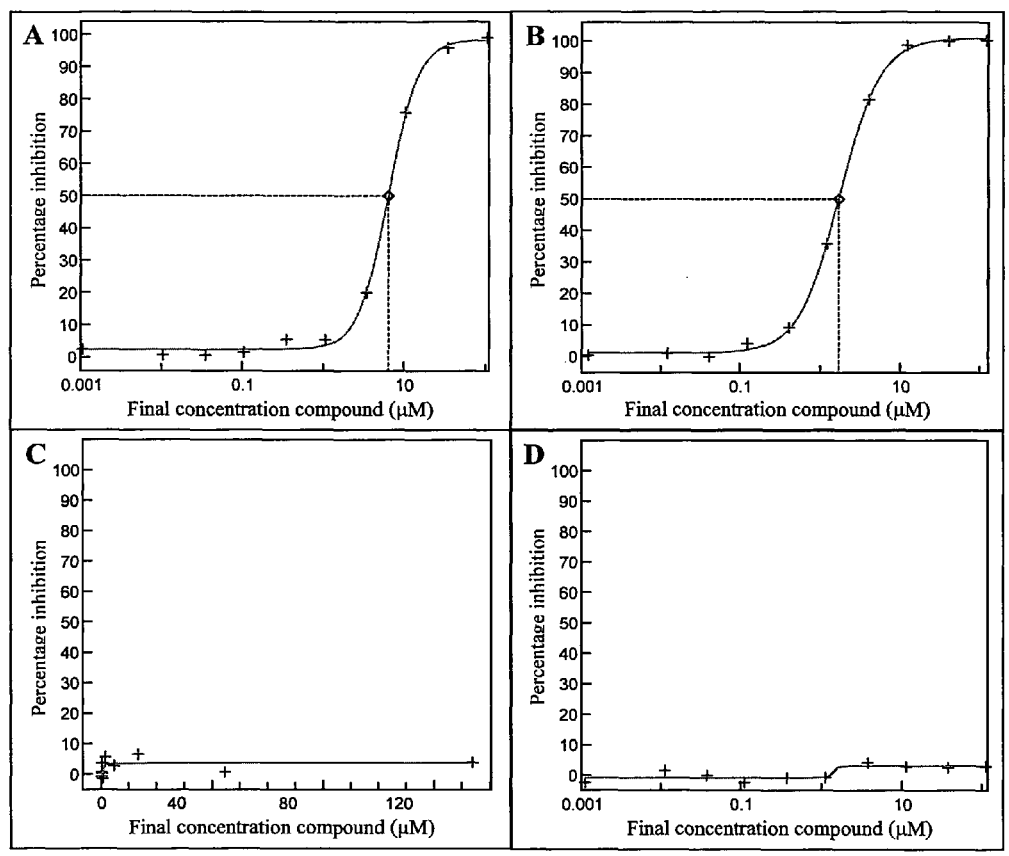
FIG. 1 illustrates inhibition curves from the PPTB screen for four presumptive inhibitors of *A. fumigatus* PPTB.

1. Knock Out of PPTB in *Aspergillus fumigatus*

1.1 Introduction

To determine the importance of PPTB in *A. fumigatus* the gene was knocked out, i.e., disrupted by directed mutagenesis. Since *A. fumigatus* is naturally haploid, a diploid strain was first created by protoplast fusion of two colour mutant haploids, giving rise to a green diploid which could be readily distinguished from the brown and white haploids. A selectable marker (PyrG) was then introduced into one copy of the PPTB gene in the diploid strain by homologous recombination resulting in a diploid strain heterozygous for PPTB. Finally, the diploid was forced to rehaploidise, creating two types of haploid, one with the undisrupted PPTB gene which grows on normal minimal medium supplemented with uridine and uracil but cannot grow without supplementation, and one with the disrupted PPTB gene. If PPTB were not essential the haploid would grow on both supplemented and unsupplemented media; if the gene were essential this haploid could not grow on either medium.

1.2 Methods and Results

The *A. fumigatus* PPTB gene including upstream and downstream flanking regions was cloned by PCR from isolated *A. fumigatus* AF293 genomic DNA. Reddy mix Extensor PCR mastermix (Abgene) was used with the following primers:

```
                                         SEQ ID No. 1
    PPTB_KOcass F1;      GCGTTGATGCAGCTGTGTAT;

SEQ ID No. 2
    PPTB KOcass R1;      TAGCCGAGGCAAGTAGCAGT;
```

The PCR product was ligated into pGEMTEasy vector by overnight ligation at 14° C. in 1× ligation buffer with T4 DNA ligase (Promega). The reaction was transformed into Select96 cells (Promega) and transformants screened by diagnostic digest (with SphI, NotI and XbaI), confirming that PPTB had been cloned into pGEMTeasy.

pGEMTEasy_PPTB DNA was mutagenised using the EZ-TN5 bacterial transposon system (Epicentre). The EZ-TN5 transposon was liberated from pMB4zeo (SEQ ID No. 3) by digestion with PshAI and XmnI. Between the transposon mosaic ends (ME) is a PyrG construct for selection in *Aspergillus* and a zeocin resistance construct for selection in bacteria. pGEMTEasy_PPTB DNA was incubated in the presence of the EZ-TN5 transposon and the EZ-TN transposase as directed by the manufacturers instructions. The transposase reaction was stopped with ¹/₁₀ volume of 10× stop solution. 1 ul of the reaction was transformed into Genehogs electrocompetent *E. coli* (Invitrogen) by electroporation. Resulting colonies were screened by PCR to identify clones that had been disrupted within the PPTB coding sequence, using the following primers:

```
SEQ ID No. 4:
PPTBint F1:
GTTCTTGGTTTCACCTCTGC;
(binds 123 bp upstream of coding sequence)

SEQ ID No. 5:
BVK1:
GAGCCAATATGCGAGAACACCCG;
(transposon terminus)
```

-continued

```
SEQ ID No. 6:
BVK6:
CGACTACGCACTAGCCAACA;
(transposon terminus)
```

A plasmid that was positive by PCR was sent for sequencing and the insertion site was found to be between bases 368 and 369 of the PPTB coding sequence (SEQ ID No. 7).

The disrupted PPTB construct was released from pGEMTEasy by digestion with NotI and purified by agarose gel electrophoresis and gel purification on a Qiaquick column (Qiagen).

This fragment was transformed into *A. fumigatus* CDP1 by protoplast transformation and transformants screened by PCR using BVK1, BVK6 and PPTBoutcass F1 & R1:

```
SEQ ID No. 8:
PPTBoutcass F1;    TCGGTGGGTTTGATGTAATC

SEQ ID No. 9:
PPTBoutcass R1;    GACAGGCGGAGATAATGATG
```

One transformant was positive for homologous recombination at the PPTB locus, i.e., one copy of the PPTB gene had been replaced by the disrupted PPTB construct in this diploid. This transformant was subjected to rehaploidisation on SAB+5 mM uridine+5 mM uracil+1.2 µg/ml benomyl. Haploid colonies were harvested and inoculated onto SABUU (non-selective) and SAB medium (selective) and grown for 3 days at 37° C. Under non-selective conditions, brown and white haploids were observed, however, under selective conditions only diploids (green) or occasional aneuploids were observed (the aeuploids grow because they have intact copies of pptb as well as the disrupted copy; this was confirmed by PCR). PPTB was therefore seen to be essential for the growth of *A. fumigatus*.

2. Production of Recombinant *A. fumigatus* PPTB and ACP 2.1 Identification of *A. fumigatus* ACP The sequences for *A. fumigatus* PPTB and its substrate ACP are available on the public databases as Afu4g04040 and Afu1g06620 respectively. Alignment of these sequences with orthologous sequences from other organisms indicated that the PPTB sequence was correct; this is given as SEQ ID No. 10. However, the ACP sequence was found to differ considerably from other sequences and was therefore re-predicted from the genomic sequence to give an ACP sequence that obeyed the cannonical exon boundary consensus and aligned well with other ACPs. The new cDNA sequence is given as SEQ ID No. 11 and the protein sequence as SEQ ID Nos. 12.

2.2 Amplification by PCR and EK/LIC Cloning

PCR was used to generate cDNA clones encoding PPTB and ACP. Since ACP is processed after translation by the removal of ~50 amino acids from the N-terminus (in *A. fumigatus* amino acids 1-49 of SEQ ID No. 12), a truncated form of ACP was generated. PCR was performed using KOD Hot Start DNA polymerase (Novagen) to amplify DNA fragments of 489 bp corresponding to PPTB and 297 bp corresponding to ACP from *A. fumigatus* cDNA. PCR primer pairs are shown below. The annealing temperatures used were 60° C. for PPTB and 50° C. for ACP.

```
PPTB sense;
                                    SEQ ID No. 13
GACGACGACAAGATGAAACTAATTCCTTTTCCA;

PPTB antisense;
                                    SEQ ID No. 14
GAGGAGAAGCCCGGTTCAACCAGCCGCAAGCAC;

ACP1F;
                                    SEQ ID No. 15
GACGACGACAAGATGTCTGCCCCCGCCGGT;

ACP1R + stop;
                                    SEQ ID No. 16
GAGGAGAAGCCCGGTTAGTGGGCATCAGGCTGGGC;
```

The PPTB product corresponded to SEQ ID No. 7, plus the overhangs from the primers; the ACP product corresponded to SEQ ID No. 17, plus the overhangs from the primers.

PCR products were excised and purified from agarose gels, treated with T4 DNA polymerase to create complementary overhanging ends and annealed to pET30 Ek/LIC vector, as described in the Ek/LIC cloning kit manual (Novagen). NovaBlue GigaSingles competent cells were used for transformation by heat-shock. Transformation mixtures were plated on LB agar/kanamycin (30 µg/ml). Plasmid DNA was prepared from several colonies by mini-prep using the Qiaprep spin miniprep kit (Qiagen) as per manufacturer's instructions and tested for the presence of the insert by PCR using the above primers, and restriction digestion with XmnI for pET30-PPTB and BglII and SalI for pET30-ACP. All clones tested contained the relevant insert. Approximately 1 µg plasmid from PPTB and ACP clones were sent for DNA sequencing; all insert sequences were found to be error free.

After initial expression studies (see below), PPTB was found to be insoluble. PPTB cDNA was therefore cloned via HindIII/KpnI restriction sites into pET43.1 b (Novagen), which contains the NusA fusion tag to aid solubility and the ampicillin resistance gene as selectable marker. After transformation of Genehogs with the PPTB-pET43.1b construct by electroporation, four clones were identified as containing the correct insert by PCR and restriction digestion with KpnI and HindIII. Clone PPTB-43.1b-1 was sequenced and found to be error free.

2.3 Overexpression of *A. fumigatus* PPTB and ACP Fusion Proteins

BL21 (DE3) Star cells were transformed with pET30-PPTB and pET30-ACP plasmids by heat-shock and grown at 37° C. with shaking overnight in 10 ml Luria Bertani (LB) broth supplemented with kanamycin (30 µg/ml) and glucose (1% w/v). 1 ml of the overnight culture was added to 10 ml LB/kanamycin/glucose and grown with shaking at 37° C. until the optical density at 600 nm reached 0.5-1 (about 2 hours). Expression was then induced by the addition of IPTG to a final concentration of 0.5 mM and cultures were grown with shaking at 20° C. for approximately 20 hours. Bacterial cells were collected by centrifugation at 3000 rpm (2000 g) in a Falcon 6/300 centrifuge at 4° C. for 15 minutes and supernatant was discarded. Cell pellets were lysed with Bugbuster supplemented with benzonase (25 U/ml) and rLysozyme (1 KU/ml) as described in the Novagen manual. 10 µl of samples were analysed by SDS-PAGE and Coomassie staining, as described in the Novagen manual. To check whether expressed protein was soluble or present in insoluble inclusion bodies, 10 µl lysed sample was centrifuged at 16000 g at 4° C. for 15 minutes. The supernatant and pellet (resuspended in 10 μl H$_2$O) were then analysed by SDS-PAGE.

PPTB protein (21.6 k Da) was found to be only partially soluble and upon purification and storage it was observed to come out of solution. PPTB was therefore cloned into a different vector, pET43.1b (Novagen), to express PPTB as a fusion protein with NusA which is a known solubility enhancer. After further cloning into pET43.1b (see above), soluble PPTB-NusA (80 kDa) was successfully expressed by BL21 (DE3) cells after 20 hours induction with 0.5 mM IPTG at 20° C. ACP fusion protein (14.5 kDa) was successfully expressed at 20° C. after induction with 0.5 mM IPTG for 20 hours.

2.4 Purification of PPTB and ACP

PPTB and ACP were purified from large-scale (50-400 ml) cultures. The cells were lysed with Bugbuster supplemented with benzonase (25 U/ml), rLysozyme (1 KU/ml) and 10 mM imidazole as described in the Novagen manual, and debris was removed by centrifugation at 16000 g for 20 minutes at 4° C. The PPTB and ACP proteins were purified from the supernatant using Ni-NTA His Bind resin as per manufacturer's instructions (Novagen). Protein was eluted off the resin using 250 mM imidazole. The preparation was then transferred into 100 mM Tris-HCl, 10 mM MgCl$_2$, pH 7.5, using PD10 desalting columns (GE Healthcare) according to manufacturer's instructions. Fractions were analysed by gel electrophoresis.

3. *A. fumigatus* PPTB Assay Development 3.1 Introduction

Currently available assays are not suitable for the high-throughput screens that are an important part of drug discovery, because they are either too labour-intensive, or because they require multiple steps (i.e., they are not homogeneous), e.g. Lambalot & Walsh (1995) J. Biol. Chem. 270, 24658-24661; Stuible et al. (1998) J. Biol. Chem. 273, 22334-22339; EP1795608; Mofid et al. (2002) J. Biol. Chem., 277, 17023-17031.

In the present work PPTB assays used a fluorescently-labelled coenzyme A molecule (CoA-Bodipy TMR), such that PPTB activity transferred the label onto the ACP. The PPTB reaction could therefore be followed by separating the products of the PPTB reaction on an SDS-PAGE gel and illuminating with UV light to see whether the ACP band had become fluorescent. For the high-throughput screen, the PPTB assays used a fluorescence polarisation approach. This measures changes in the orientation of plane-polarized light brought about by fluorophores that undergo significant molecular motion during their fluorescence lifetime. This lifetime is defined as the period of time between absorption of an excitation photon and the emission of a photon through fluorescence. The rotation of the CoA-Bodipy TMR molecule is reduced if it binds to a molecule of significantly greater size, in this case ACP. The reduction in rotation causes a reduction in the ability of the Bodipy TMR molecule to depolarise plane-polarised light, which can be measured.

3.2 Generation of Bodipy TMR-Labelled CoA (CoA-Bodipy TMR)

Fluorescent coenzyme A was generated by coupling Bodipy TMR iodoacetimide (Molecular Probes) to the terminal —SH group of coenzyme A. 60 mM coenzyme A stock was prepared in sterile ddH$_2$O. 15 mM Bodipy TMR iodoacetimide stock was prepared in DMSO immediately prior to use and protected from light. CoA was added to the Bodipy TMR iodoacetimide to give a molar ratio of between 1.5:1 and 1:1 Bodipy TMR:CoA. The volume was then increased by addition of 2.5 ml of buffer (100 mM Bis-Tris, 10 mM MgCl$_2$ pH7.5) per mg Bodipy TMR used in the labelling reaction, the sample vortexed and incubated on ice for 30 minutes, then at room temperature for 10 minutes. Excess unreacted Bodipy TMR iodoacetimide label was removed by extraction with ethyl acetate; 10 ml ethyl acetate was added, mixed by vortexing, the layers allowed to separate and the organic layer removed. This was repeated until the ethyl acetate remained clear and did not fluoresce under UV light. Approximately 1.5 ml of an intensely pink solution remained per mg Bodipy TMR iodoacetimide used in the labelling reaction. Before storage at −80° C. the CoA-Bodipy TMR was diluted 1:5 in assay buffer and aliquoted.

3.3 PPTB Assay

Preliminary studies showed that recombinant PPTB was able to label recombinant ACP (resolved on SDS-PAGE gel) in the presence of magnesium ions and CoA-Bodipy TMR, indicating that the PPTB was functional. The labelling reaction was inhibited by the addition of EDTA. Further experiments were carried out using fluorescence polarization to optimise the PPTB assay for high-throughput screening.

4. High-Throughput Screen for Inhibitors of *A. fumigatus* PPTB 4.1 Equipment

High-throughput fluorescent polarization screens for PPTB inhibitors were carried out in black, flat-bottom 384 well plates using the following equipment: Thermo Labsystems Multidrop 384 machine (Multidrop® 384) with dispensing cassette and plate adapter; Tecan Genesis Freedom and Tecan Te—Mo automated liquid handling robot with 235 μl tip head, plus appropriate PC/base unit/software; PerkinElmer Minitrak automated liquid handling robot with 235 μl tip head plus appropriate PC/base unit/software; and PerkinElmer Fusion-Alpha-FP HT plate reading spectrophotometer plus appropriate FP filters (Excitation filter 540 nm; Emission filter 580 nm, both filters with 20 nm bandwidth).

4.2 Stock Solutions

Buffer A: 62.5 mM Bis-Tris buffer (pH 6.75), 12.5 mM MgCl$_2$. The final concentrations in the assay were 50 mM Bis-Tris and 10 mM MgCl$_2$.

CoA-Bodipy TMR-ACP mix: 11.6 ml ACP (3.421 mg/ml) plus 1854.7 μl CoA-Bodipy TMR stock (see Section 3.2 above) was made up to 529.9 ml with Buffer A at 4° C.

PPTB enzyme: PPTB enzyme was typically used at 50 to 100 ng total protein/well; enzyme was used at a concentration that gave reaction linearity with respect to both time and protein concentration. This had to be determined for each enzyme batch. Immediately prior to the stage of the screen requiring enzyme addition, an aliquot of enzyme was thawed on ice and washed into the relevant volume of Buffer A.

Stop Reagent; 60 mM EDTA pH8.0.

4.3 Running the PPTB Screen

Assays were carried out in black, flat-bottomed 384-well plates. Initially compound libraries were screened to identify potential hits: Solutions of compounds were first dispensed into wells to give a final concentration in the assay of 0.02 mg/ml in 1% v/v DMSO in water (equivalent to 50 μM for a compound with a molecular weight of 400 daltons). 20 μl PPTB enzyme solution was then added to wells; no-enzyme control wells received 20 μl Buffer A. 20 μl CoA-Bodipy TMR-ACP mix was added to all wells and plates incubated for 30 minutes at room temperature. The reaction was terminated by the addition of 25 µl Stop Reagent, after which plates were read in a spectrophotometer. Compounds giving an inhibition of at least 80% were considered potential hits.

Screen quality was measured using the parameters Z', % CV and W, which are defined as follows, where "SD" stands for standard deviation, "100% control" is a 384 microwell plate where all wells contain the uninhibited reaction, and "0% control" is a 384 microwell plate where all wells contain a completely inhibited reaction, or no enzyme:

$Z'=1-((3SD\ 100\%\ control+3SD\ 0\%\ control)/(mean\ 100\%\ control-mean\ 0\%\ control));$ $\%\ CV=(Standard\ deviation\ of\ data\ from\ whole\ plate/mean\ of\ data\ from\ whole\ plate)\times 100;$ this can be calculated for plates with are 0% control (% $CV_{0\%}$) or plates with are 100% control (% $CV_{100\%}$).

$W=(100\%\ control-0\%\ control)/\sqrt{((SD\ 100\%\ control)^2+(SD\ 0\%\ control)^2))}$ Surprisingly, it was found that the reaction products in the assay plates were stable for at least five days after the assay: Thus after 1 hour the assay quality parameters had the following values; Z'=0.83, % $CV_{100\%}$=3.4% and W=22.9; while after 5 days Z'=0.77, % CV=2.3% and W=17.9. Also, when the assay was carried out using unlabelled coenzyme A, the $IC_{50}$ for CoA was 6.02 µM on day one, and 5.90 µM after 105 hours. This stability enabled large numbers of compounds to be screened and large numbers of plates to be read. A long stability time is of particular importance when fluorescence polarization is used as a detection method since individual wells take longer to read than with, for example, simple absorbance spectrophotometry. For 10,000 compounds, the initial stage of the assay, from the dispensing of compounds from stocks to the stopping of the reaction, typically took 7 hours. Reading plates took 60 hours, although 10 hours may be possible.

Potential hits were then tested in a secondary screen over a concentration range of 40 µg/ml-400 pg/ml (final concentration; equivalent to 100 µM-1 nM for a compound of 400 daltons molecular weight). Sample data are given in FIG. 1 showing secondary screen results for four compounds identified from the high-throughput screen. Two of the compounds (A and B) were found to be inhibitors, with good $IC_{50}$ values, while two (C and D) were found to be inactive. Typically, compounds with an $IC_{50}$ of less than or equal to 10 µM were considered good inhibitors, and it was considered preferable that the inhibition curve was sigmoidal and that the 5% to 95% inhibition range was within a two log span of inhibitor concentration.

5. Essentiality of PPTB in Candida albicans

5.1 Introduction

The Candida albicans homolog of A. fumigatus PPTB is CaO19.4812. C. albicans is a diploid organism so to determine the importance of PPTB in C. albicans both alleles must be considered. The strategy was to knockout one allele completely and to place the other allele under the control of the regulatable promoter MET3. The MET3 promoter is downregulated by the presence of methionine and cysteine (Care et al, 1999 Molecular Microbiology 34, 792-798).

Two rounds of homologous transformation were performed; the first to insert the MET3 promoter directly in front of the PPTB start codon, the second to disrupt the remaining allele by directed mutagenesis. The C. albicans triple auxotroph SN76 (ura3/arg4/his1) was used in the experiments. Promoter replacement was carried out using a construct consisting of the MET3 promoter and a URA3 marker. Directed mutagenesis was performed using a construct with an ARG4 marker. If PPTB is essential for growth of the fungus, when the remaining copy of the gene is downregulated by the presence of methionine and cysteine the mutant should not grow. However, in the absence of methionine and cysteine, PPTB will be expressed and the mutant should grow.

5.2 Methods and Results

The promoter replacement construct was made by fusion PCR. Firstly three PCR products were prepared using KOD DNA polymerase (Novagen), annealing temperatures of 55° C. and extension temperatures of 68° C. 391 bp of the 5' region of the PPTB gene were amplified from SN76 genomic DNA using primers PPTBF (SEQ ID No. 30) and PPTBMIDR (SEQ ID No. 31). A URA3-MET3 construct of 2733 bp was prepared using the primers URA3MET3F (SEQ ID No. 32) and URA3MET3R. (SEQ ID No. 33). The template was the pMET3 plasmid consisting of the CIP10 vector (Murad et al, 2000 Yeast 16, 325-327) with the C. albicans MET3 promoter (Care et al, 1999 Molecular Microbiology 34 (4), 792-798) inserted downstream of the URA3 gene in place of the RPS10 locus. The first 394 bp of the PPTB coding sequence was amplified from SN76 genomic DNA using primers PPTBMIDF (SEQ ID No. 34) and PPTBR (SEQ ID No. 35).

```
SEQ ID No. 30:
PPTBF:
CACGGTTTCACCAGTGTCTG

SEQ ID No. 31:
PPTBMIDR:
GATCTAGGCTTGGCCAAGTCGGCCGCTGGAAAAATTTCCCCGAGA

SEQ ID No. 32:
URA3MET3F:
CGGCCGACTTGGCCAAGCCTAGATC

SEQ ID No. 33:
URA3MET3R:
TGGGGAGGGTATTTACTTTTAAATA

SEQ ID No. 34:
PPTBMIDF:
TATTTAAAAGTAAATACCCTCCCCAATGCCAAAAGTAGGCACTGT

SEQ ID No. 35:
PPTBR:
_CCTTCTGACGAAGTACTGTAGCAA
```

The PCR products contained 25 bp overlapping sequence at their termini allowing the products to be fused together in a final fusion PCR reaction using PPTBF (SEQ ID No. 30) and PPTBR (SEQ ID No. 35) primers with the 3 PCR products present in the reaction. A 3543 bp product was obtained. This product was used to transform C. albicans SN76 using the lithium acetate method (Walther and Wendland, 2003 Current Genetics 42, 339-343) followed by incubation on SD agar (1× yeast nitrogen base without amino acids+2% glucose+2% bacto agar)+arginine (0.2 mM)+histidine (0.2 mM) plates for 3 days at 30° C. The resulting transformants were inoculated onto SD agar+arginine+histidine and incubated for 4 days. Colonies were screened for the correct insertion of the MET3 promoter by PCR. One of these mutants was selected for the second round of transformation. This conditional heterozygote was named PPTB#2.

To knockout the second allele a second transformation construct was made by PCR using a CaARG4 construct containing the ARG4 marker (Dennison et al, 2005 Fungal Genetics and Biology 42, 737-748) as a template and long primers PPTBARGF (SEQ ID No. 36) and PPTBARGR (SEQ ID No. 37) where 20 bp corresponded to plasmid binding areas and 100 bp were homologous to the target insertion area. KOD DNA polymerase was used, with an annealing temperature of 55° C. and elongation temperature of 68° C.

SEQ ID No. 36:
PPTBARGF:
GGAAATTTTTCCAGCATCGAGTTAGTAGCTCTCTGTACCTTAATATCTAC

TACATGTGATGCCAAAAGTAGGCACTGTATTGGGTATAGGTGTTGATATC

CCAGGGTTTTCCCAGTCACG

SEQ ID No. 37:
PPTBARGR:
CTTTAGATTTGATAAACCTTCTGACGAAGTACTGTAGCAATTACAAGAGA

ATCATCATGTGAGATACTAAGATGGAACTCTTCATCAGACAATTTGTATC

ACTAAAGGGAACAAAAGC

A 2486 bp product was obtained consisting of the ARG4 marker flanked by 100 bp of the PPTB gene 5' and 3' flanking regions. This product was used to transform PPTB#2 using the lithium acetate protocol followed by incubation on SD agar+histidine for 3 days at 30° C. Resulting transformants were re-inoculated onto SD agar+histidine. Selected colonies were inoculated into SD medium, incubated overnight at 30° C. and genomic DNA isolated using the MasterPure Yeast DNA extraction kit (Epicentre Biotechnologies). Five PCR reactions were performed to identify the correct insertion of both transformation constructs and absence of the wild type allele using the following primer pairs: PPTBUP (SEQ ID No. 38) and URAMET31NTR (SEQ ID No. 39) (expected product size 982 bp); PPTBD (SEQ ID No. 40) and URAMET31NTF (SEQ ID No. 41) (expected product size=1310 bp); PPTBUP (SEQ ID No. 42) and ARGINTR (SEQ ID No. 43) (expected product size=1667 bp); PPTBD (SEQ ID No. 40) and ARGINTF (SEQ ID No. 44) (expected product size=1789 bp); PPTBF (SEQ ID No. 30) & PPTBR (SEQ ID No. 35) expected product size for wild type only=785 bp).

SEQ ID No. 38:
PPTBUP:        GCTGTTCCCAAGTTTGGTGT

SEQ ID No. 39:
URAMET3INTR:   TGCTACTGGTGAGGCATGAG

SEQ ID No. 40:
PPTBD:         CAAGACCCATCACAATGTCG

SEQ ID No. 41:
URAMET3INTF:   ATTGCTGTGGATCACGTGC

SEQ ID No. 42:
PPTBUP:        GCTGTTCCCAAGTTTGGTGT

SEQ ID No. 43:
ARGINTR:       GCCCATCTAATAGGTTGAGC

SEQ ID No. 44:
ARGINTF:       GCAATTCTTGAACGAGCACA

Figure 3:
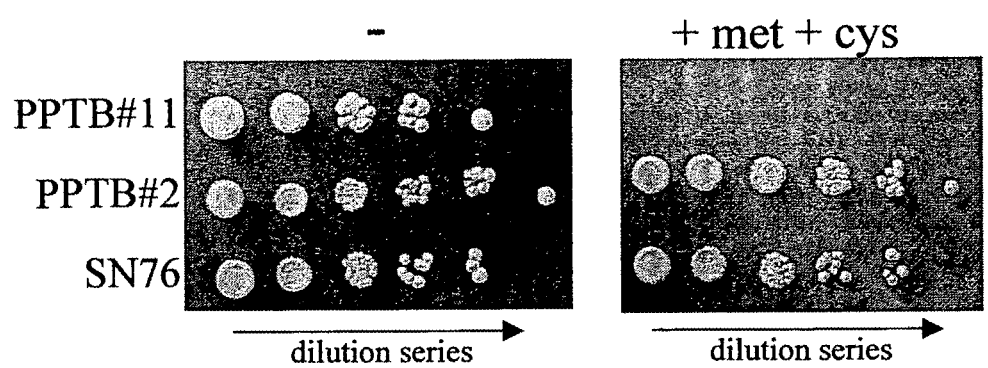
FIG. 3 shows the growth of *C. albicans* PPTB mutants in the presence and absence of methionine and cysteine.

One of the transformants was shown to have the desired genotype where one allele was under the control of the MET3 promoter and the second allele had been knocked out completely. This conditional null mutant was termed PPTB#11. PPTB#11 was grown up in SD media+histidine overnight. The OD600 was measured and adjusted in SD+histidine to an OD600 of 0.1. 5 µl of this culture and subsequent 5-fold dilutions were inoculated onto SD agar+histidine+arginine+uridine media with and without 2.5 mM methionine and 2.5 mM cysteine. The SN76 parental strain and PPTB2 were used as controls. Plates were incubated at 30 C for 4 days and the results are shown in FIG. 3. After incubation the SN76 and PPTB#2 had grown in the presence and absence of methionine and cysteine. The conditional null mutant PPTB#11 had grown only in the absence of methionine and cysteine thereby showing that CaO19.4812 is a gene essential for growth in *C. albicans*.

6. Production of Recombinant *C. albicans* PPTB and ACP 6.1 Cloning, Expression and Purification of *C. albicans* PPTB Candida albicans PPTB, CaO19.4812 is a single-exon gene; the DNA sequence is given in SEQ ID No. 18, the protein sequence in SEQ ID No. 19. Although *C. albicans* translates the CTG codon as serine instead of the leucine seen in most other organisms, there are no CTG codons in this gene. The *C. albicans* PPTB gene was generated by PCR from *C. albicans* genomic DNA using primers SEQ ID No. 20 (SK_CPPTB-F) and SEQ ID No. 21 (SK_CPPTB-R) and KOD Hot Start DNA polymerase (Novagen).

SEQ ID No. 20:
SK_CPPTB-F:
GAC GAC GAC AAG ATG CCA AAA GTA GGC ACT GTA T

SEQ ID No. 21
SK_CPPTB-R;
GAG GAG AAGCCC GGT TTA GAT TTG ATA AAC CTT CT;

The PCR product was treated with T4 DNA polymerase, ligated into pET43.1 and transformed into Novablue cells. Colonies were checked for the correct insert by PCR and restriction digest. The resulting pET43-PPTB construct was used to transform BL21 cells. Small scale induction of protein expression and sequencing of the PPTB insert was carried out to identify an error-free clone suitable for protein production.

To produce *C. albicans* PPTB for assays, cells containing pET43.1-PPTB were used to innoculate 12 ml LB/ampicillin (100 µg/ml)/glucose (1%) and the culture grown overnight at 37° C. 4 ml of this was then added to 100 ml LB/ampicillin/glucose, and the culture grown for 2 hours 20 minutes until an $OD_{600}$ of 0.747 was reached. IPTG was then added to a final concentration of 0.3 mM and the culture incubated at 15° C. overnight with shaking. Cell pellets were harvested by centrifugation and one 50 ml pellet lysed with 3 ml BugBuster, 25 U/ml benzonase, 1 KU/ml lysozyme, 10 mM imidazole, after which the lysates were clarified by centrifugation at 16000 g for 20 minutes at 4° C. Further purification steps using Ni-NTA His Bind resin were carried out as described in section 2.4.

Assays for *C. albicans* PPTB activity using *A. fumigatus* ACP as a substrate gave a poor signal. Recombinant *C. albicans* ACP was therefore produced to determine whether the *C. albicans* enzyme requires *C. albicans* ACP as its substrate.

6.2 Cloning, Expression and Purification of *C. albicans* ACPs

BLAST searches showed that *C. albicans* has two ACPs, CaO19.8439 (ACPg), and CaO19.9975 (ACPe), although ACPg resembles the single ACP of *S. cerevisiae* more closely. SEQ ID Nos. and location of mature N-termini after cleavage (see 2.2 above) are given in Table 1. Both are single-exon genes with no CTG codons.

TABLE 1

The ACPs of *C. albicans*

| Identifier | *C. albicans* gene | Sequence type | Start of mature sequence after cleavage | SEQ ID No. |
|---|---|---|---|---|
| ACPg | CaO19.8439 | DNA | Base 76 | SEQ ID No. 22 |
| ACPg | CaO19.8439 | Protein | Amino acid 26 | SEQ ID No. 23 |
| ACPe | CaO19.9975 | DNA | Base 166 | SEQ ID No. 24 |
| ACPe | CaO19.9975 | Protein | Amino acid 56 | SEQ ID No. 25 | cDNA for the *C. albicans* ACPs was generated by PCR using KOD-Hot Start Polymerase, *C. albicans* gDNA and the following primers:

```
ACPg; CaO19.8439 primers
                                          SEQ ID No. 26
SK_GoodACP-F;
GACGAC GAC AAG ATG GTT GCC CCA CCA ATT TC;

SEQ ID No. 27
SK_GoodACP-R;
GAG GAG AAG CCC GGT TTA TTT AGA TTC TTC TTT GT;

ACPe; CaO19.9975 primers
                                          SEQ ID No. 28
SK_EvilACP-F;
GAC GAC GAC AAG ATG AGT GCC TTC CCA GAA TT;

SEQ ID No. 29
SKEvilACP-R;
GAG GAG AAG CCC GGT TTA ACA AGA ATC TGG TTG AG;
```

PCR products were treated with T4 DNA polymerase, ligated into pET30, transformed into Novablue cells, and plated onto LB/kanamycin (30 µg/ml). Colonies were tested by PCR to check for an insert, then DNA was prepared and checked further by restriction digestion and sequencing. Error-free DNA was transformed into *E. coli* BL21 cells and test inductions were found to give soluble proteins of the correct molecular weight.

For both ACPs BL21 cells containing pET30-ACP were grown overnight in LB/kanamycin (30 µg/ml)/glucose (1%). 3 ml of the culture was then inoculated into 50 ml LB/kanamycin/glucose and grown for 2 hr at 37° C. after which protein expression was induced by the addition of IPTG (0.5 mM final concentration), after which cells were incubated at 20° C. overnight with shaking. The bacterial pellet was then collected by centrifugation and the protein purified as above (section 2.4). ACP samples were exchanged into 100 mM Tris, 10 mM $MgCl_2$, pH 7.5 using a PD10 desalting column.

6.3 *C. albicans* PPTB Assay.

PPTB assays were set up using PPTB and ACPs from both *A. fumigatus* and *C. albicans* and CoA-Bodipy TMR, with the reaction products resolved on an SDS-PAGE gel and visualised under UV light. The *C. albicans* PPTB pantetheinylated ACPg strongly, but ACPe and the *A. fumigatus* ACP were pantetheinylated weakly. The *A. fumigatus* PPTB was able to pantetheinylate both *A. fumigatus* ACP and ACPg whereas ACPe was pantetheinylated weakly. Therefore, the *C. albicans* PPTB requires the *C. albicans* ACPg for correct function.

7. High-Throughput Screen for *C. albicans* PPTB Inhibitors

Figure 2:
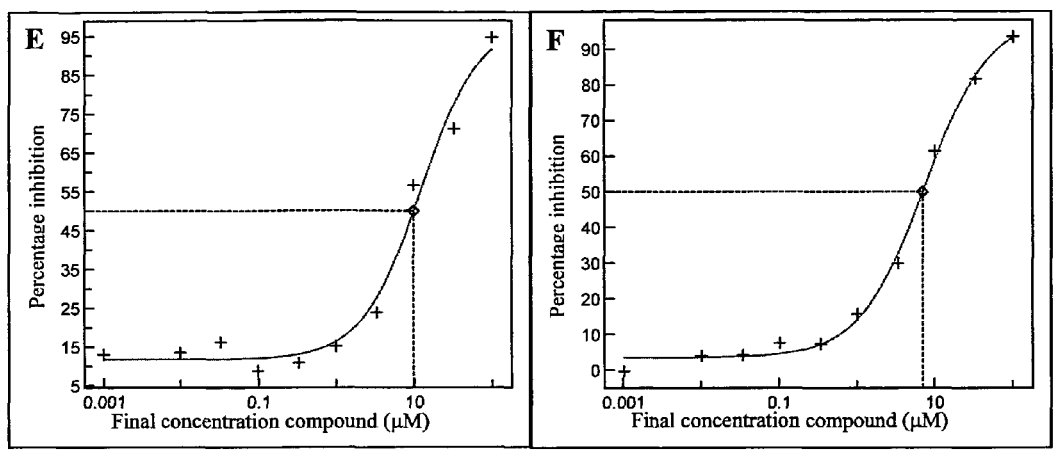
FIG. 2 illustrates inhibition curves from the PPTB screen for two presumptive inhibitors, of *C. albicans* PPTB.

Screens for inhibitors of *C. albicans* PPTB were carried out as described above for *A. fumigatus* PPTB (section 4), using the *C. albicans* PPTB and *C. albicans* ACPg, with adjustments to protein concentrations. Two compounds active against the *A. fumigatus* PPTB were tested against the *C. albicans* enzyme; results are shown in FIG. 2. Both compounds were found to be good inhibitors of the *C. albicans* enzyme; compound E was found to have an $IC_{50}$ of 9.8 µM and compound F an $IC_{50}$ of 7.1 µM.

The invention claimed is:

1. A method of identifying an antifungal agent comprising determining whether a candidate compound inhibits:
   (i) a phosphopantetheinyl transferase B (PPTB) protein which comprises the sequence shown by SEQ ID NO. 10 or SEQ ID NO. 19,
   (ii) a protein which has at least 90% identity with (i), wherein inhibition of (i) or (ii) indicates that the candidate substance is an antifungal agent, and wherein (i) or (ii) have PPTB activity.

2. The method according to claim 1 which comprises determining whether the candidate compound is able to inhibit the transfer of a phosphopantetheinyl group to acyl carrier protein (ACP) by (i) or (ii).

3. The method according to claim 2 wherein detection of the transfer is carried out by measuring a change in the fluorescence properties of a fluorophore attached to the ACP.

4. The method according to claim 2 or 3 wherein the ACP molecule is:
   (i) a fungal ACP,
   (ii) a fungal ACP from the same fungus as the PPTB protein or the protein which has at least 90% identity with the PPTB protein,
   (iii) ACP which comprises the sequence shown by SEQ ID NO. 12, SEQ ID NO. 23, or SEQ ID NO:25,
   (iv) ACP which is encoded by SEQ ID NO:17; or
   (v) an ACP protein which has at least 90% identity with (iii) or (iv).

5. The method according to claim 4, wherein the ACP molecule, is of a fungus which expresses more than one ACP, and at least of one of the ACP molecules expressed by the fungus is not a substrate for PPTB.

6. The method according to claim 2 wherein detection of the transfer is carried out using fluorescence polarization.

7. The method according to claim 1 which is carried out under the conditions of:
   about 50 mM Bis-Tris, and/or about 10 mM $MgCl_2$, and/or
   at about pH 6.75, and/or
   with about 1% v/v DMSO, and/or
   at a PPTB enzyme concentration such that the enzyme activity is in a linear range with respect to time and protein concentration, and/or
   incubated for 20-40 minutes, and/or
   incubated at about room temperature, and/or
   where the stop reagent is about 60 mM of EDTA at about pH8.0, and/or
   where the assay has a Z' value of $\geq 0.70$, and/or
   where the assay has a % $CV_{100\%}$ value of $\leq 4\%$, and/or
   where the assay has a W value of >15.

8. The method according to claim 1 wherein in the method an ACP product is formed which is stable for at least up to 5 days such that after 5 days Z'$\geq$0.70, % $CV_{100\%}\leq$4% and W>15.

9. The method according to claim 1 which is a high throughput method in which at least 10,000 different compounds are screened.

10. The method according to claim 9 wherein at least 10,000 different compounds are screened in less than 70 hours.

11. The method according to claim 1 which comprises determining the inhibition curve of the candidate compound.

12. The method according to claim 11, which further comprises selecting the compound based on:
   whether the $IC_{50}$ is less than or equal to 10 μM, and/or
   whether the inhibition curve is sigmoidal and the range of 5% to 95% inhibition is within a two log span of the inhibitor concentration.

* * * * *